(12) United States Patent
Jendoubi

(10) Patent No.: US 10,031,130 B2
(45) Date of Patent: *Jul. 24, 2018

(54) DEVICE FOR HIGH THROUGHPUT DETECTION OF CERVICAL DISEASE

(71) Applicant: MILAGEN, INC., Emeryville, CA (US)

(72) Inventor: Moncef Jendoubi, San Francisco, CA (US)

(73) Assignee: MILAGEN, INC., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/412,887

(22) Filed: Jan. 23, 2017

(65) Prior Publication Data

US 2017/0146523 A1 May 25, 2017

Related U.S. Application Data

(63) Continuation-in-part of application No. 12/973,061, filed on Dec. 20, 2010, now Pat. No. 9,551,700.

(51) Int. Cl.
*G01N 33/543* (2006.01)
*G01N 33/53* (2006.01)
*G01N 33/574* (2006.01)
*B01L 3/00* (2006.01)

(52) U.S. Cl.
CPC ........ *G01N 33/5304* (2013.01); *B01L 3/5085* (2013.01); *G01N 33/57411* (2013.01)

(58) Field of Classification Search
None
See application file for complete search history.

(56) References Cited

U.S. PATENT DOCUMENTS

| | | | | |
|---|---|---|---|---|
| 9,551,700 B2 * | 1/2017 | Jendoubi | ............ | G01N 33/5008 |
| 2012/0269721 A1 * | 10/2012 | Weng | ................ | A61K 49/0002 |
| | | | | 424/1.11 |
| 2012/0282595 A1 * | 11/2012 | Cheng | .............. | G01N 33/56983 |
| | | | | 435/5 |

* cited by examiner

*Primary Examiner* — Gary Counts
(74) *Attorney, Agent, or Firm* — VLP Law Group LLP; Kurt T. Mulville, Esq.

(57) ABSTRACT

The present invention is a device for high-throughput detection, screening and disease management of cervical disease. The device is comprised of a solid support featuring multiple well-separated areas, each accommodating a patient sample, leading to simultaneous evaluation of patient samples. The device enables cytological staining, cervical Pap staining, and immunochemical staining using antibodies or combination of antibodies which are capable of binding to biomarkers that are overexpressed in cancer including in cervical carcinoma and dysplasia, as compared to normal controls. The device can be used in either manual or automated mode, and applied to any biological fluid or cell suspension from any biological specimen in view of a variety of cell biology assays, and in view of detection and screening of cervical and other diseases.

10 Claims, 14 Drawing Sheets

DEVICE FOR HIGH THROUGHPUT DETECTION OF CERVICAL DISEASE

PRIORITY

This application is a continuation-in-part of U.S. patent application Ser. No. 12/973,061, now U.S. Pat. No. 9,551,700.

FIELD OF INVENTION

The field of the invention is cervical disease detection and screening, using a novel multiwell device and methods thereof.

BACKGROUND

Cervical cancer incidence and mortality. Cervical cancer is the second most commonly diagnosed malignancy and the third leading cause of cancer death in women worldwide. There were 555,100 new cases and 309,800 deaths estimated in 2007, 83% of which occurred in the developing world (American Cancer Society, ACS Global Cancer Facts and Figures, 2007).

In the US in 2010 there were an estimated 12,200 new cases of invasive cervical cancer and an estimated 4,210 deaths from cervical cancer (American Cancer Society, ACS Cancer Facts & Figures, 2010; Jemal A, et al., Cancer statistics, 2010, CA Cancer J Clin 60:277-300, 2010). Since its establishment in 1957, Pap smear has become a routine screening test in the US. As a result, cervical cancer incidence rates have decreased in both white and African American women, pre-invasive lesions of the cervix are detected far more frequently than invasive cancer, and mortality rates have steadily declined as well over the past several decades.

Cervical cancer etiology and pathology. Infection with human papillomavirus (HPV) is a primary etiologic factor in cervical cancer. The magnitude of risk association is greater than that for smoking and lung cancer (Unger E R, Barr E, Human papillomavirus and cervical cancer, in Emerg Infect Dis 10:2031-2032, 2004). Among the 200 HPV types known, HPV16/18 are the most commonly associated to cervical cancer, with more than a 200-fold increased risk (Castellsague X, et al., Worldwide human papillomavirus etiology of cervical adenocarcinoma and its cofactors: implications for screening and prevention, J Natl Cancer Inst 5:303-315, 2006).

However most HPV infections disappear spontaneously and only a small percentage progress to CIN (cervical intraepithelial neoplasia) or CIS (carcinoma in situ). Other risk factors contributing to cervical cancer may be immunosuppression, high parity, smoking, and nutritional factors, as well as long-term use of oral contraceptives (WHO/ICO Information Centre on HPV and Cervical Cancer, Summary report on HPV and cervical cancer statistics in Brazil, 2007; ACS, 2010).

Cervical cancer comprises two major types: squamous cell carcinoma (75%) and adenocarcinoma (20%), affecting the squamous cells and the glandular cells of the cervix epithelium respectively (WHO/ICO, 2007).

The Bethesda system classifies precancerous cervical lesions in: i) atypical squamous cells of undetermined significance (ASCUS); ii) low grade squamous intraepithelial lesions (LSIL) or cervical intraepithelial neoplasia (CIN I), characterized by mild dysplasia; iii) high grade squamous intraepithelial lesions (HSIL) or cervical intraepithelial neoplasia, including carcinoma in situ (CIN II, CIN III/CIS) characterized by moderate to severe dysplasia. Note that LSIL/HSIL nomenclature refers to cervical lesions detected by cytology, while CIN nomenclature refers to dysplasia determined upon histological analysis of biopsied cervical tissues (WHO/ICO, 2007).

CIN I rarely (1%) develop into cancer, and mostly return to normal even if untreated; CIN II carry a risk of progression into cancer of 16% by two years and 25% after five years, if left untreated. CIS is cervix confined cancer that will develop into invasive cervical cancer (ICC) over a period of 10 to 12 years. One year and five year relative survival for cervical cancer patients in the US is 88% and 72% respectively, while the 5-year survival rate for patients diagnosed with localized cervical cancer is 92% (ACS, 2010).

Pre-cancerous CIN lesions may be treated by electrocoagulation, cryotherapy, $CO_2$ laser ablation, or local surgery (Campion M, Preinvasive disease. In: Practical Gynecologic Oncology Third Edition. Eds: Berek J S, Hacker N F, Lippincott, Williams & Wilkins, Philadelphia, USA, pp 271-343, 2000; ACS, 2007). Invasive cervical cancers are treated with surgery, radiation or both, as well as chemotherapy in selected cases. Symptoms, often abnormal vaginal bleeding, do not appear until cancer has developed.

Cervical cancer screening. Pap smear screening in developed countries has undoubtedly contributed to the decrease in cervical cancer incidence and mortality, due to early detection of cervical lesions. The Pap test is a cytological staining of cervical cells collected through a simple procedure performed in the doctor's office. Cells are either directly smeared on a slide, then fixed and stained (conventional Pap smear), or first rinsed in a liquid preservative solution to thin mucous and eliminate cell debris, prior to preparing a slide (liquid-based cytology, LBC). In both cases, the slides are read by a cytopathologist.

The Pap smear and LBC methods are based on subjective visual readings of cell morphologies, and have a limited sensitivity of 50% and high susceptibility to intra and inter-individual variability (Boulet G A V, et al., Human papillomavirus in cervical cancer screening: important role as biomarker, Cancer Epidemiol Biomarkers Prey 17:810-817, 2008). 50,000 to 300,000 cells per slide may be read to find 20-30 potentially abnormal cells, and double reading is often required. These tests require highly trained staff and adequate laboratories, making the tests labor-intensive and expensive. So, in addition to limited sensitivity, Pap test is also a relatively costly procedure requiring infrastructure and pathology expertise.

The relatively low sensitivity results in a high false-negative rate, mostly due to inadequate sampling and improper slide preparation. Efforts have been made to address these issues and technologies have been developed that either improve on the way slides are prepared and analyzed, or on the reading burden. The development of LBC technology (ThinPrep, Hologic; SurePath, BD) has provided more standardized method of sampling. For example, the ThinPrep2000 processor purifies cell samples from contaminating blood, bacteria, mucus, and other inflammatory material, prior to depositing it on a slide that will be analyzed by a cytotechnologist. This method detects 65% more LSIL in the general population than conventional Pap smear, and reduces by >50% the number of inadequate cell samples, and provides the ability to perform additional tests out of the same vial. Furthermore, computerized imaging systems now identify suspicious cells that are subsequently examined by a pathologist.

In conclusion, automated slide preparation and automated reading methods have reduced the burden of the analysis, as well as the intra and inter-individual variability of evaluation. Nonetheless, while improving test accuracy, these technologies contribute to increased high-tech infrastructure and cost required for cervical screening, clearly not to the advantage of low infrastructure settings. And still to date the Pap test remains a "reading" based screening, requiring appropriate infrastructure and human resources.

The etiologic relationship between HPV and cervical cancer has been exploited for the development of molecular technologies for viral detection to overcome limitations of cytologic cervical screening. HPV testing by DNA amplification is now used to complement equivocal Pap smears, to triage high risk patients and address them to cytology, and as follow-up after CIN treatment (Boulet, 2008). Currently HPV testing serves as a surrogate end point for cervical cancer screening. However, it has also been suggested for primary screening, particularly in women over age 30, followed by cytology screening if HPV positive (Smith R A, Cokkinides V, Eyre H J. American Cancer Society Guidelines for the Early Detection of Cancer, CA Cancer J Clin 55:31-44, 2005).

According to the ACS recommendations (Smith, 2005), cervical cancer screening should be done every year with Pap test or LBC. If Pap smear is abnormal and reveals ASCUS, HPV testing is done, and if positive, women are referred to colposcopy. If Pap smear reveals LSIL or HSIL, women are immediately referred to colposcopy. Colposcopy is the microscopic examination of the cervix upon acetic acid or Lugol's stain to reveal abnormal cells, which can be in turn biopsied. Women over age 30 who have had three normal Pap test results in a row may get screened every 2-3 years with cervical cytology alone, or every 3 years with an HPV DNA test plus cervical cytology. Women over age 70 and older who have had three or more normal Pap test in a row, and no abnormal Pap test in the last 10 years, may stop screening (Smith, 2005).

Tissue and serum biomarkers. With the aim to improve Pap smear accuracy and complement current cervical screening, potential biomarkers of preneoplastic cervical lesions and cervical cancer have been described.

Antigen Ki-67 is a large nuclear protein, which is expressed in proliferating cells (Goodson W H., et al. The functional relationship between in vivo bromo-deoxyuridine labeling index and Ki-67 proliferation index in human breast cancer, Breast Cancer Res Treat 1998 May; 49 (2): 155-164; Scholzen T., et al. The Ki-67 protein: from the known and the unknown [review], J. Cell Physiol 2000; 182:311-22). Ki-67 is preferentially expressed during all active phases of the cell cycle (late G1-, S-, G2-and M-), but absent in resting cells (G0-). In diagnostic histopathology, antibodies to Ki-67 are used to grade proliferation rates of tumors (Cattoretti G., et al. Monoclonal antibodies against recombinant parts of the Ki-67 antigen (MIB1 and MIB3) detect proliferating cells in microwave-processed formalin-fixed paraffin sections. J Pathol 1992; 168:357-63). Ki-67 immunostaining using the commercially available antibody MIB-1 has been evaluated as an adjunct test to increase diagnostic accuracy of cervical squamous intraepithelial lesions (LSIL and HSIL; Pirog et al. Diagnostic accuracy of cervical low-grade squamous intraepithelial lesions is improved with MILB-1 immunostaining, Am J Surg Pathol 26:70-75, 2002). Indeed it is reported that there is considerable interobserver variation in the diagnosis of LSIL. MIB-1 immunostaining was found to be more sensitive and specific than HPV testing.

It has been shown that minichromosome maintenance (MCM) proteins, and particularly MCM-2, MCM-5 and MCM-7, are useful for the detection of cervical disease including dysplasia and cancer (Williams et al., Proc Natl Acad Sci U.S.A. 95:14932-14937, 1998; Freeman et al., Clin Cancer Res. 5:2121-2132, 1999), as demonstrated on conventional cervical smears or by immunohistochemical staining of cervical tissues. Recent results using an HPV-transgenic mouse model have shown that MCM-7 further appears to be a specific marker for the detection of high-grade cervical disease by immunochemistry (Brake et al., Cancer Res. 63:8173-8180, 2003; Malinowski et al., Acta Cytol. 43:696, 2004; U.S. Pat. No. 7,632,498 Malinowski et al., 2009).

Cyclin-dependent kinase inhibitor 2A (CDKN2A), also known as p16(INK4a) is a cell cycle regulator overexpressed in cervical preneoplastic lesions harboring HPV16/18 and in cervical cancer. p16(INK4a) overexpression is due to functional inactivation of retinoblastoma Rb protein by HPV E7 protein. p16(INK4a) overexpression is thus related to active HPV gene expression, rather than viral presence only. It has thus been proposed that overexpression of p16(INK4a) may be used as a marker for persistent high-risk HPV infection and detection of high-grade squamous epithelial lesions (HSIL; Klaes et al. Overexpression of p16 (INK4a) as a specific marker for dysplastic and neoplastic epithelial cells of the cervix uteri, Int J Cancer 92:276-284, 2001; Agoff et al., p16(INK4a) expression correlates with degree of cervical neoplasia: a comparison with Ki-67 expression and detection of high-risk HPV types, Mod Pathol 16:665-673, 2003; Von Knebel Doeberitz et al, 2004, U.S. Pat. No. 6,709,832).

Immunohistochemical detection of p16(INK4a) in cervical biopsies is in routine use for discriminating between HPV and non-HPV associated lesions (Redman R, et al., The utility of p16(Ink4a) in discriminating between cervical intraepithelial neoplasia 1 and non-neoplastic equivocal lesions of the cervix, Arch Pathol Lab Med 132:795-799, 2008), and as surrogate marker of high-risk HPV infection (Mulvany N J, et al., Diagnostic utility of p16INK4a: a reappraisal of its use in cervical biopsies. Pathology 40:335-344, 2008). Furthermore, p16INK4a immunostaining of ThinPrep cervical specimens is being evaluated for its ability to assist in the identification of high-grade intraepithelial lesions, as assessed by follow-up biopsies and high-risk HPV DNA testing (Meyer et al., Evaluation of p16INK4a expression in ThinPrep cervical specimens with the CINtec p16INK4a assay, Cancer, 111:83-92, 2007; Doeberitz et al, 2007, U.S. Pat. No. 7,306,926). Finally, an ELISA-based procedure for detecting p16(INK4a) using protein lysates of exfoliative cervical cells has been reported to yield higher sensitivity and specificity for dysplasia and cancer than ThinPrep Test (Ding L, et al., ELISA Test to detect CDK2A (p16(INK4a) expression in exfoliative cells: a new screening tool for cervical cancer, Mol Diagn Ther 12:395-400, 2008).

In conclusion, the use of antibodies against specific biomarkers of cervical cancer and cervical preneoplastic lesions may increase the accuracy of current cervical screening. There is a consensus in the field that misinterpretation and interobserver discrepancies are common, especially in the LSIL cytology category. Indeed antibody immunostaining represents an "objective test", and insofar may serve as an adjunct to the morphological interpretation offered by the pathologist. Antibodies against specific biomarkers could thus assist in the diagnostic interpretation of LSIL by increasing accuracy of histopathology or cytology-based diagnosis.

Among circulating biomarkers, squamous cell carcinoma antigen serum levels have been found to correlate with tumor stage, tumor size, residual tumor after treatment, recurrent or progressive disease, and survival in squamous cervical carcinoma (Gaarenstroom K N, Bonfrer J M G. NACB, National Academy of Clinical Biochemistry: Guidelines for the use of tumor markers in cervical cancer, 2007). SCC antigen is a group of glycoproteins with molecular weight~45 KDa, belonging to the family of serine protease inhibitors. There are in fact two genes, SSC1 and SSC2, both located on chromosome 18q21.3, coding for the neutral and acidic isoform respectively. The neutral form is detected in both normal and malignant epithelial cells, whereas the acidic isoform is found in tumor cells and in the sera of cancer patients with well-differentiated squamous cell carcinoma (Kato H, et al., Heterogenous distribution of acidic TA-4 in cervical squamous cell carcinoma; immunohistochemical demonstration with monoclonal antibodies, Jpn J Cancer Res 78:1246-1250, 1987). SSC1 and SSC2 are almost identical, only differing in their reactive loops. There is evidence they regulate proteolytic events in both normal and pathological processes, yet have distinct biological functions (De Bruijn H W A, et al., The clinical value of squamous cell carcinoma antigen in cancer of the uterine cervix, Tumor Biol 19: 505-516, 1998). Elevated levels of SCC have also been found in patients with squamous cell carcinoma of other organs (vulva, vagina, head and neck, lung) as well as in patients with benign diseases of the skin (psoriasis, eczema), lung (sarcoidosis), liver and kidney. However, according to the NACB recommendations (Gaarenstroom, 2007), SCC is not a sufficiently sensitive biomarker for cervical cancer screening, and its clinical utility in prognosis and monitoring response to treatment needs further evaluation.

In conclusion, there is a need to improve the accuracy, performance and cost of current cervical screening. The device and methods of the present invention have utility application as novel cytology-based high throughput cervical screening.

SUMMARY OF THE INVENTION

The present invention discloses a novel device and methods thereof for the detection and screening of cervical disease in patient cervical samples.

The "multiwell" device of the present invention consists of a solid support featuring multiple well-separated circular areas, each accommodating a patient sample, leading to simultaneous evaluation of multiple patient samples in view of cervical disease detection and screening, using the methods of the present invention.

The methods of the present invention first comprise conventional cytological stains applied to the novel multiwell device, including the conventional hematoxylin or hematoxylin and eosin (H&E) staining, and the conventional Pap staining. Thus, the device and method of the present invention have utility application in the high-throughput detection, screening and disease management of cervical disease.

The present invention encompasses the application of the device and methods of the present invention to patient specimen derived from any biological fluid or tissue. Insofar the present invention provides utility application in the analysis, detection, diagnosis, disease management and screening of a variety of diseases and conditions at a variety of organ sites, beyond gynecological diseases.

The device and methods of the present invention can also find utility application in a variety of other cell-based and cytology assays, as well as cell biology assays including but not limited to the screening of drugs and small molecule compounds, and the study of cellular pathways.

Preneoplastic, dysplastic and malignant cervical cell samples are rare. Therefore, in a preferred embodiment of the present invention, an experimental condition is established that mimicks a patient sample for cervical cancer screening, by mixing normal cervical cells with cells from a cervical cancer cell line, that are grown together in co-culture. This co-culture example is then used throughout to illustrate the methods of the present invention. The use of authentic Thin Preps, the most common cervical samples currently used for cervical cancer screening, and other forms of patient cervical samples are all encompassed by the present invention.

The present invention also provides a novel immunostaining method of patient cervical samples using the multiwell device. Resorting to the mixture of cervical cancer cells and normal cervical cells to mimick a patient cervical sample, a specific antibody targeting an antigen that is overexpressed in cervical cancer cells is used to stain the latter among normal cervical cells. The present invention takes advantage of the use of specific antibodies to pinpoint a few cancer cells in a mixture of normal cells, thus increasing diagnostic accuracy over the visual evaluation of cell morphologies by the pathologist.

Encompassed by the present invention is the use of other antibodies or combination of antibodies against biomarkers or combination of biomarkers that are associated to preneoplastic, neoplastic or dysplastic cervical cells. Use of antibodies against such biomarkers would greatly improve current Pap screening sensitivity.

Finally the present invention details a novel method for cervical disease detection and screening which is practiced on a cell suspension in solution. Said cell suspension is a mixture of normal cervical cells and cells from a cervical cancer cell line, as described above, an experimental condition mimicking a patient sample for cervical screening. Authentic ThinPrep samples are encompassed in the present invention. In this preferred embodiment, cell staining is described with an anti-p16(INK4a) antibody, which localizes to the cell nucleus and cytoplasm in the cancer cell type used. Other antibodies or combination of antibodies against biomarkers or combination of biomarkers that are associated to preneoplastic, neoplastic or dysplastic cervical cells are encompassed by the present invention, and would greatly improve current Pap screening sensitivity.

The latter embodiment further provides the ability to quantify the specific antigen-antibody reaction, in turn facilitating and potentially automating the whole process of cervical cancer screening. In the present example a colorimetric reaction is used, but other detection systems are encompassed by the present invention. Immunostaining based on colorimetric reading of cell reactivity represents an accurate, cost-effective, and user-friendly improvement over visual evaluation of staining intensities and cell morphologies by the pathologist.

Kits for practicing the methods of the invention are further provided.

It is understood by those skilled in the arts, that the device and methods of the present invention can be practiced in a manual mode, or modified accordingly into a semi-automated, or fully automated procedure.

In conclusion, the present invention provides several improvements and utility applications thereof over current cervical screening procedures: i) single to multiple high-throughput capability, ii) increased accuracy in diagnostic interpretation as compared to evaluation of cell morphology alone, due to further use of specific antibodies, and finally iii) cost-effective, user-friendly and quantitative measurement of antigen-antibody reaction. Moreover, the features of the present device and its applications to cervical disease screening would greatly benefit cervical screening in developing countries and low to medium resource settings.

BRIEF DESCRIPTION OF THE DRAWINGS

FIGS. 2B-2D: 10×). The results show that cytological staining can be successfully performed in the high-throughput multiwell device of the present invention.

FIGS. 3F-3G: 40×). The results show that the use of antibodies improves recognition of cancer cells, as compared to morphology evaluation alone.

TABLE I

Immunostaining of cancer cells among normal cervical cells in solution using elisa-type format and commonly used antibodies. As in FIG. 3, cervical cancer cells are mixed with normal cervical cells from a patient ThinPrep, except that in this case a given and increasing number of cancer cells is used (200, 300, 400, 600, 800, 1200 cell per well). Furthermore, this experiment is performed in a 96-well plate format rather than in the multiwell device, and the immunostaining is practiced with the cell suspension alternate method, as described in detail in Example 4. Immunostaining is as described in FIG. 3 with duplicate samples, except that substrate used for detection is soluble, such as TMB, and that antigen-antibody reaction is evaluated by a colorimetric plate reader at 450 nm. Controls include blank with no cell, and blank with cells and no primary antibody. $OD^1$ and $OD^2$ are readings executed on the whole cell suspension sample (which contains a light cell pellet), or on the supernatant only of the cell suspension, respectively.

| Sample # | Cancer cell # | $OD^1$ | $OD^2$ |
| --- | --- | --- | --- |
| 1 | 200 | 0.713 | 0.676 |
| 2 | 200 | 0.759 | 0.746 |
| 3 | 300 | 0.904 | 0.984 |
| 4 | 300 | 0.776 | 0.751 |
| 5 | 400 | 0.921 | 0.809 |
| 6 | 400 | 0.749 | 0.707 |
| 7 | 600 | 1.039 | 0.93 |
| 8 | 600 | 0.995 | 1.045 |
| 9 | 800 | 1.11 | 1.002 |
| 10 | 800 | 1.1 | 0.944 |
| 11 | 1200 | 1.235 | 1.005 |
| 12 | 1200 | 1.186 | 0.982 |

DESCRIPTION OF PREFERRED EMBODIMENT

The present invention pertains to the disclosure of a novel device and methods thereof for the detection and screening of cervical disease in patient cervical samples.

Multiwell Device. The "multiwell" device of the present invention consists of a solid support featuring multiple well-separated circular areas, each accommodating a patient sample, leading to simultaneous evaluation of multiple patient samples in view of cervical disease detection and screening, using the methods of the present invention.

Insofar, the novelty of the device is that it allows performing cervical sample evaluation in multiple samples simultaneously, contrary to conventional Pap smear screening or current Thin Prep analysis, whereby individual samples are smeared on a glass slide, and stained using the conventional Papanicolau staining.

Figure 1:
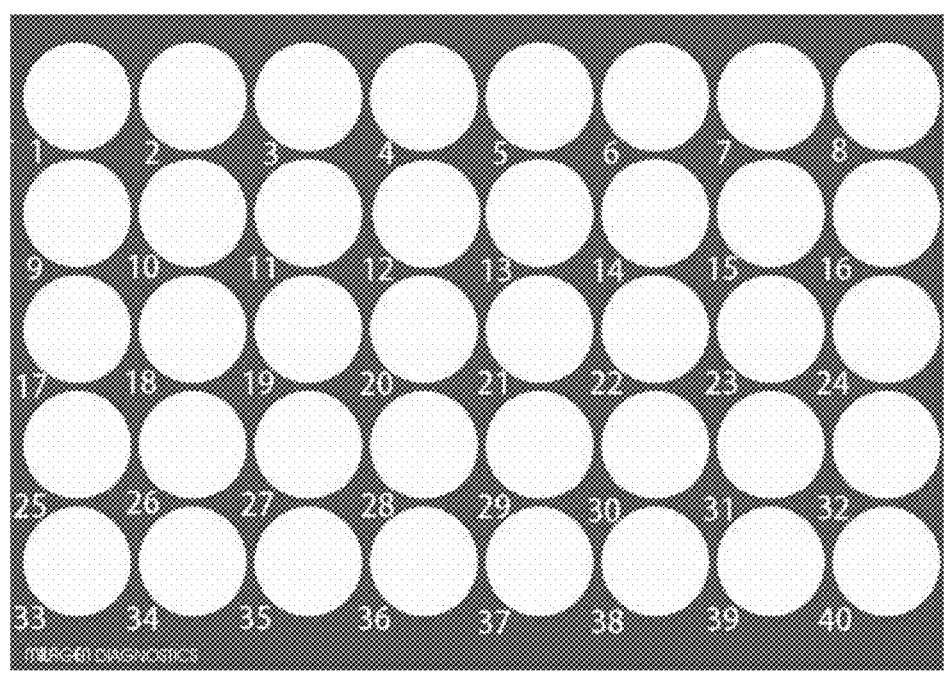
FIG. 1: Drawing of multiwell device. The drawing illustrates the multiwell device of the present invention. Prototype is 90×130×1 mm featuring numbered (1-40) circular areas (or wells) of 15 mm in diameter. Other formats are encompassed by the present invention, such as, but not limited to: 6, 12, 24, 48, 96, 384-well or any other size, provided well diameter is compatible with scope of the relevant cell-based assay, and overall device can be easily mounted and read under microscope.
Figure 2A:
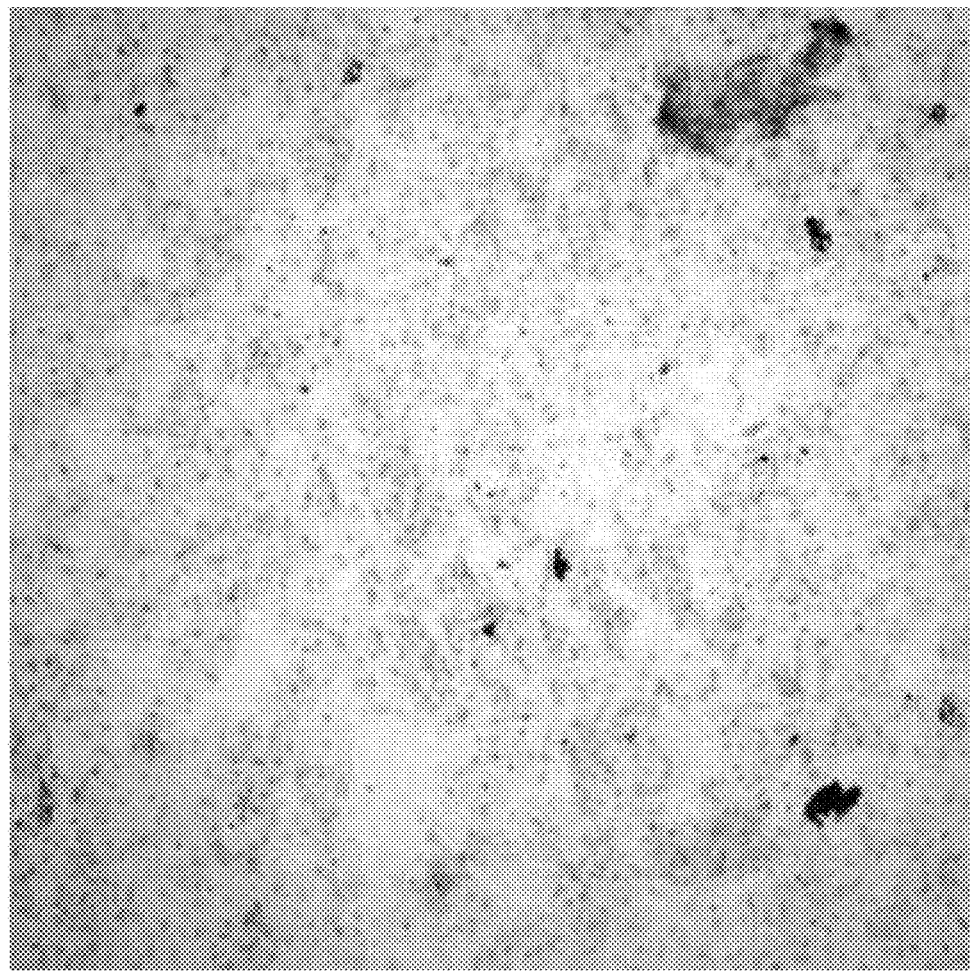
FIGS. 2A-2D: Hematoxylin staining of normal cervical cells using multiwell device. As described in detail in Example 1, cervical cells from normal patient cervical samples, i.e. 250 µl of a Thin Prep, are deposited in each of the 15 mm diameter circular areas of the multiwell device. Multiple samples can thus be evaluated simultaneously. Cells are air dried at RT and rinsed with PBS. Cleared from excess cell debris, cells are ready for any cytological stain. Herein, hematoxylin staining is shown for four different samples (2A-2B) of the multiwell device. The device is rinsed with ddH2O, and samples are covered with a few drops of weak Mayer's hematoxylin solution for 1-2 min, then rinsed with tap H2O or bluing solution to color nuclei in blue. The device is observed under microscope at different magnifications (FIG. 2A: 4×.
Figure 2B:
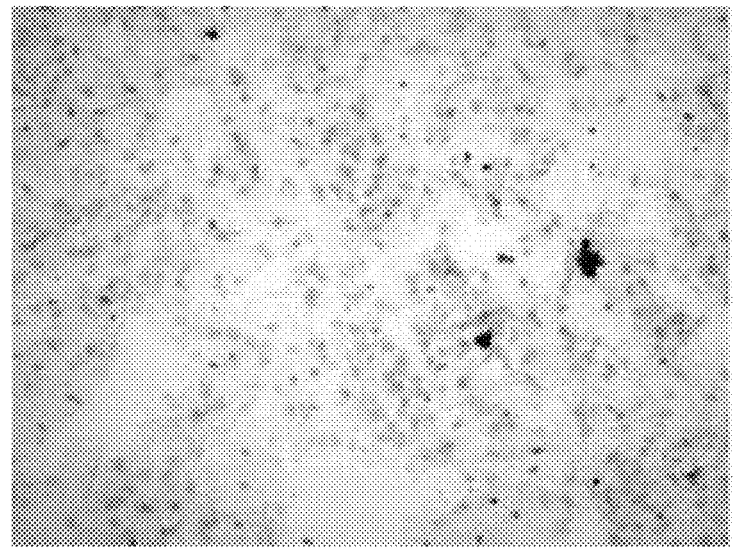
Figure 2C:
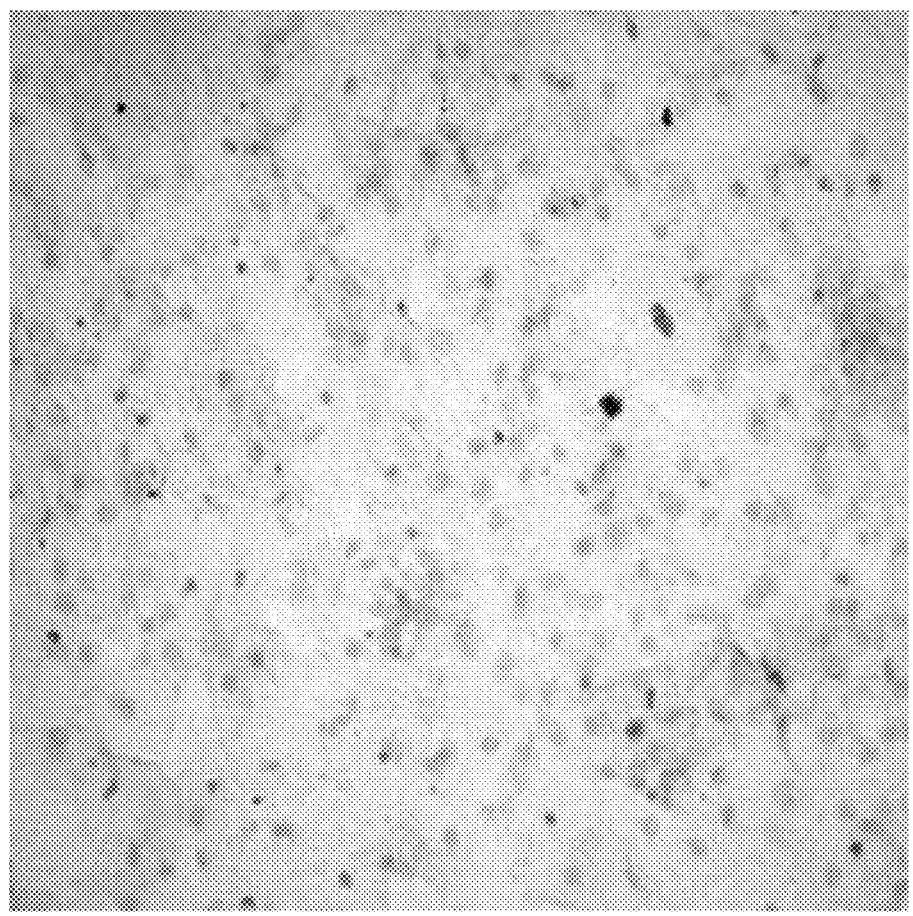
Figure 2D:
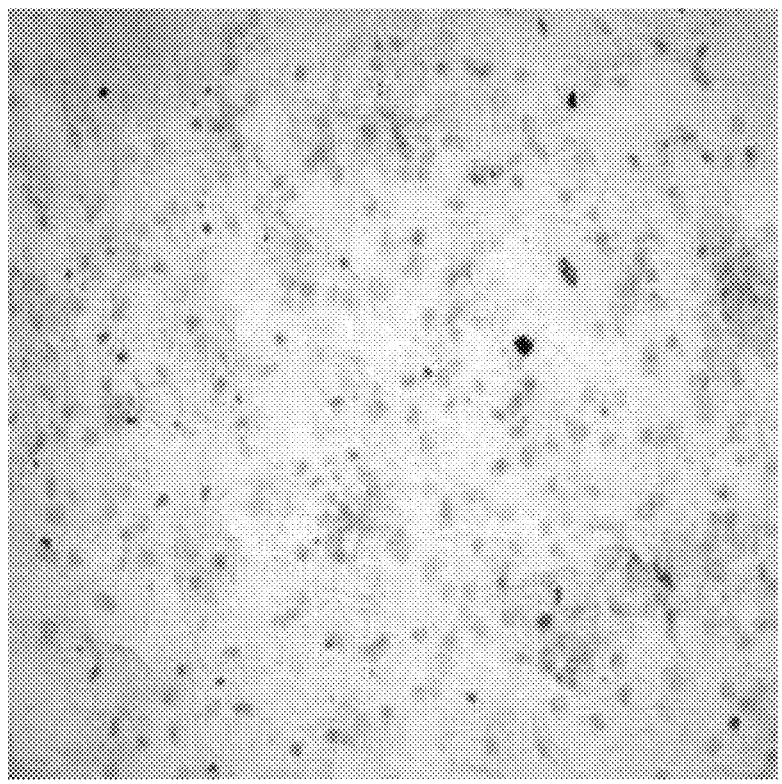
Figure 3A:
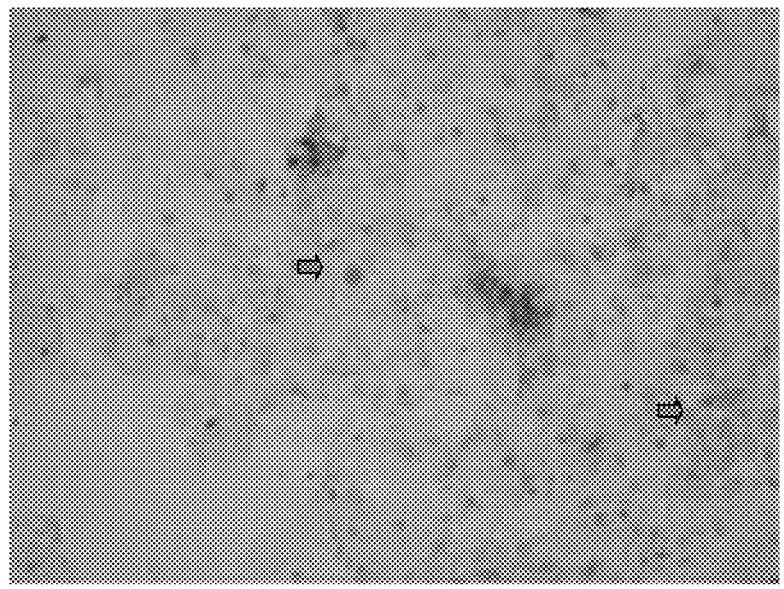
FIGS. 3A-3G: Immunostaining of cancer cells among normal cervical cells using multiwell device and commonly used antibodies. Cervical cells from a normal patient cervical sample (Thin Prep) are mixed with SiHa cervical cancer cells in a co-culture experiment mimicking a patient sample for cervical cancer screening, as described in Examples 2 and 3, in a multiwell device format. Then immunostaining with specific antibodies is performed. Specifically, a constant amount of normal cervical cells is deposited in the multiwell, while some cancer cells (i.e. enough to be visualized in a field for the purpose of the example) are subsequently layered, and grown ON at 37° C. Duplicate, triplicate or quadruplicate samples enable reproducibility testing. Cells are treated for peroxidase inactivation prior to antibody staining. P16(INK4a) monoclonal antibody is added as primary antibody at 1 µg/ml in PBS. Incubation is carried out 1 hr at 37° C. For detection, anti-mouse IgG biotinylated secondary antibody (diluted to 1 µg/ml in PBS) is added and incubated 1 hr at 37° C., followed by Streptavidin-linked to horseradish peroxidase (also diluted to 1 µg/ml in PBS and incubated 1 hr at 37° C.). The reaction is developed by addition of DAB substrate, producing a brown staining, and stopped with PBS containing azide. Multiwell device is evaluated under microscope at different magnifications (FIGS. 3A-3E: 10×.
Figure 3B:
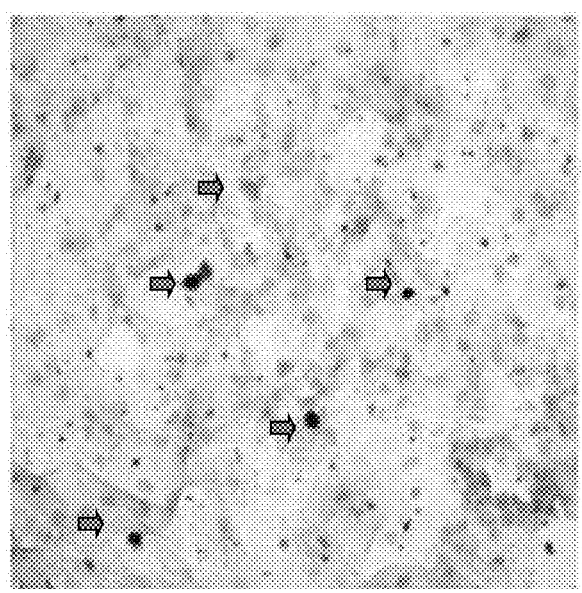
Figure 3C:
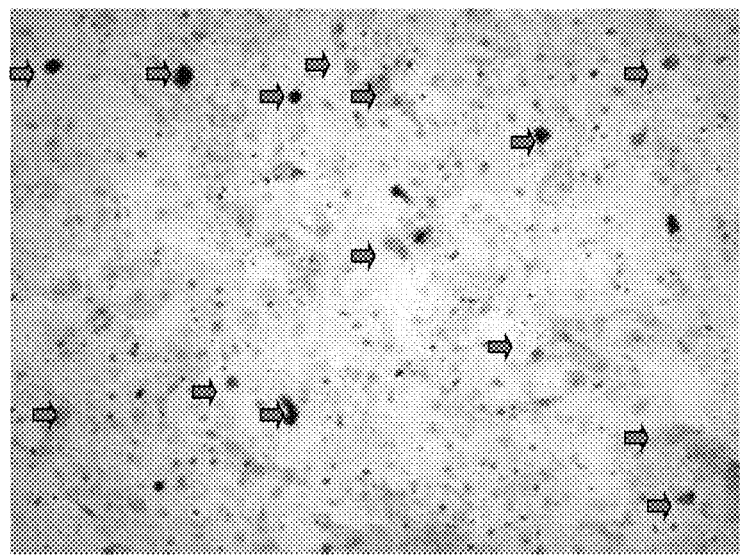
Figure 3D:
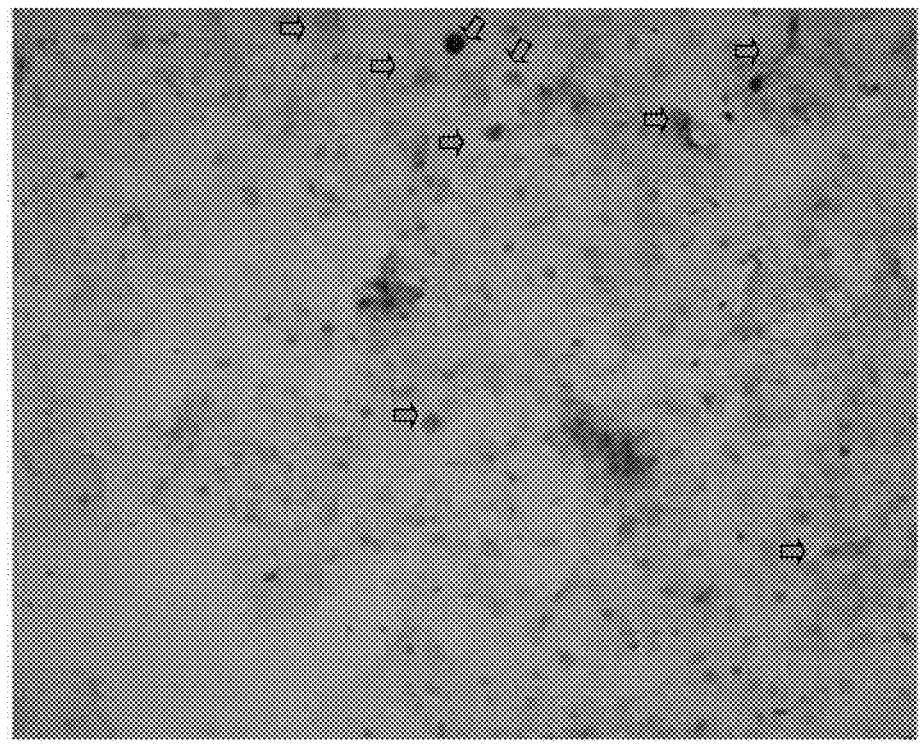
Figure 3E:
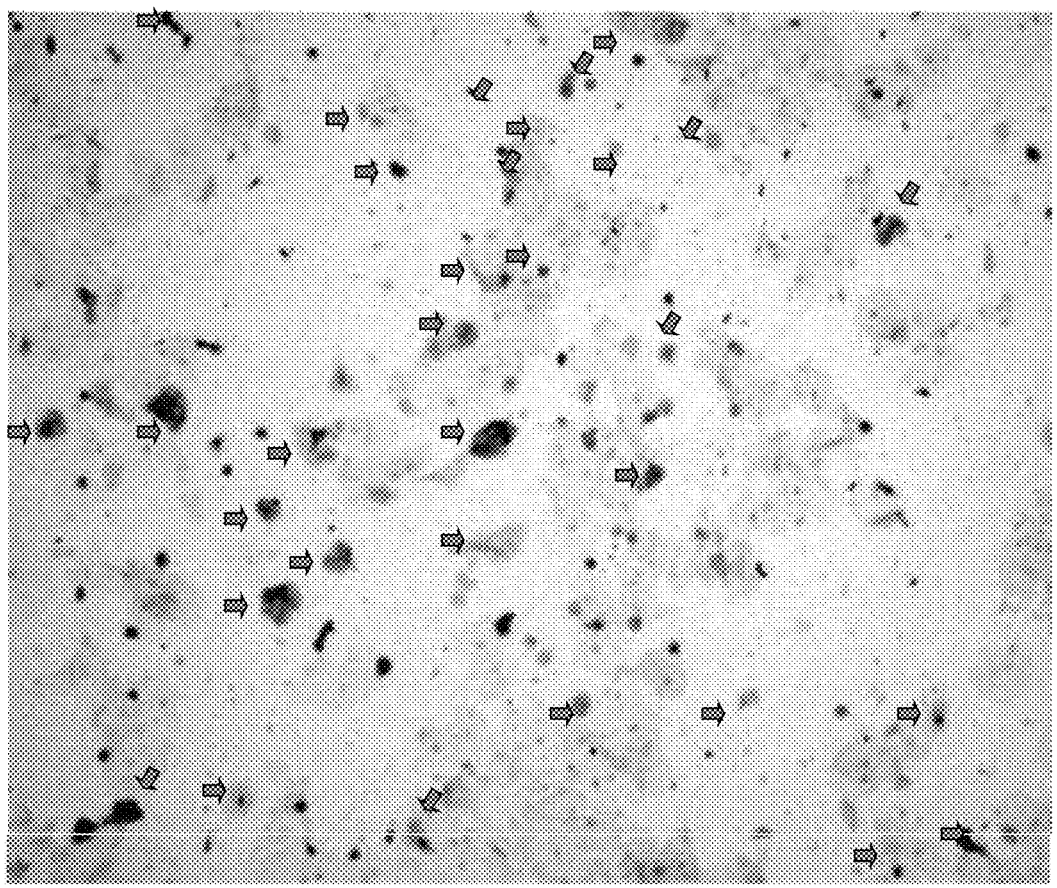
Figure 3F:
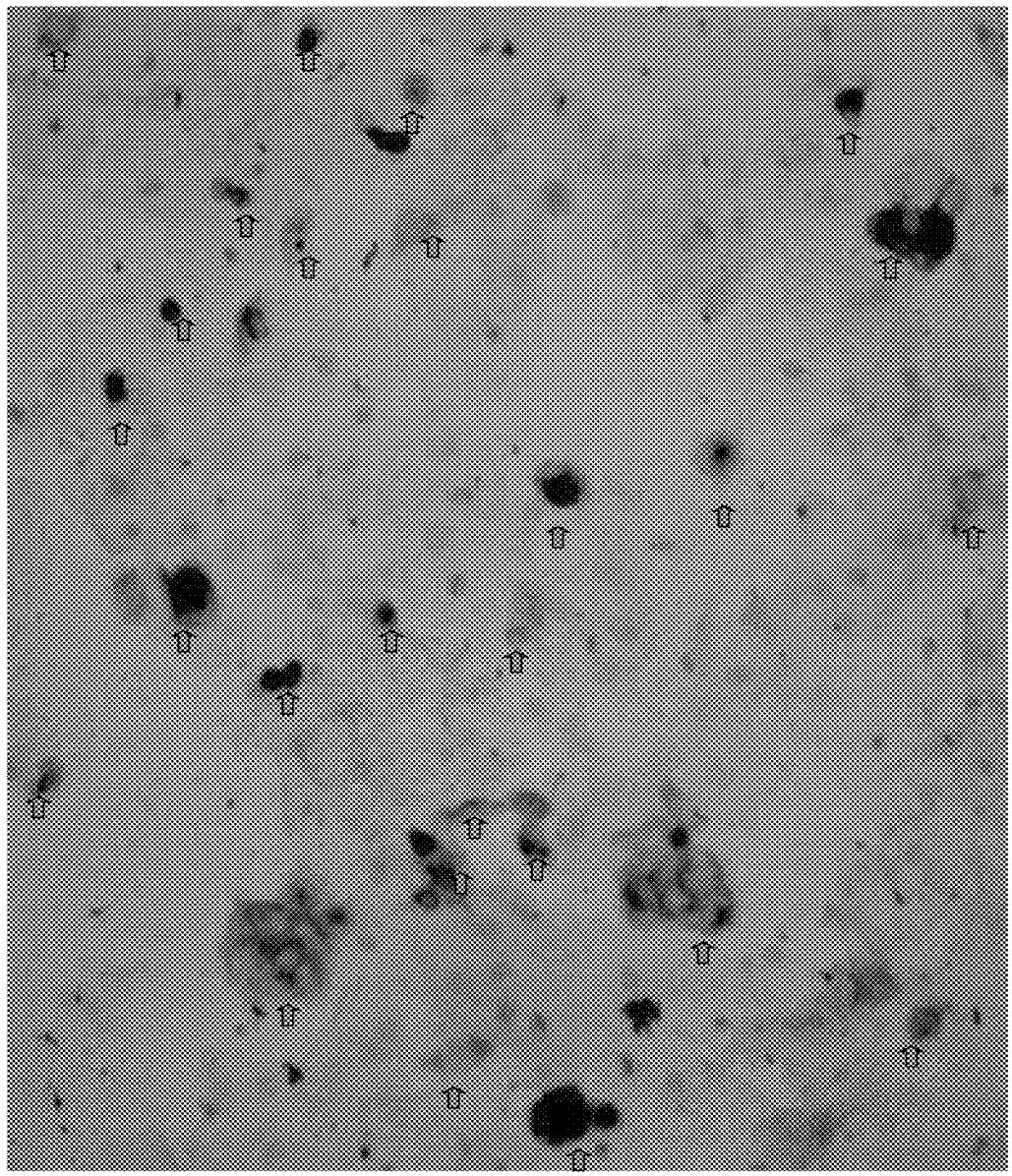
Figure 3G:
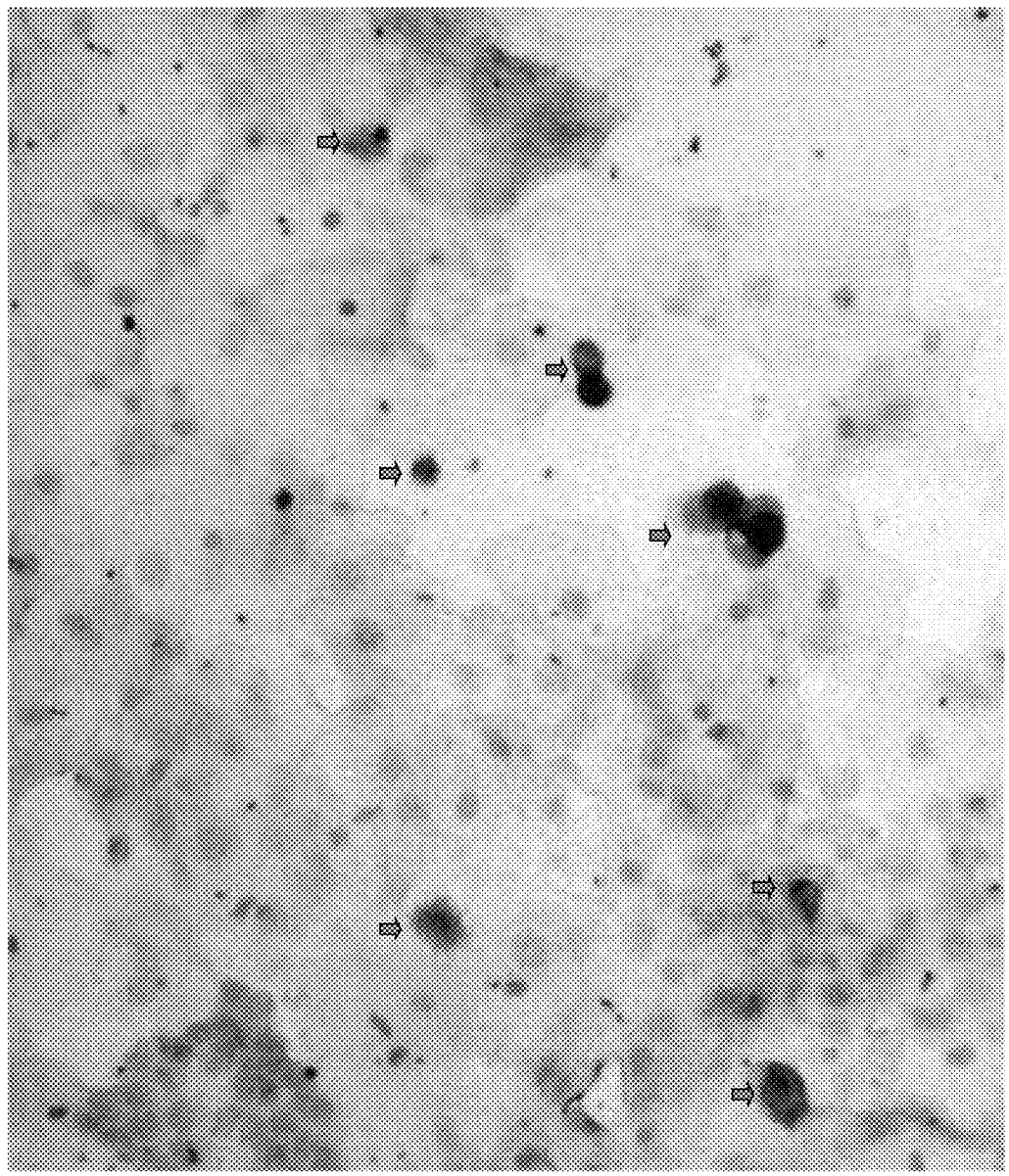

FIG. 1 illustrates the prototype multiwell device of the present invention featuring 40 numbered (1-40) circular areas (or wells) of 15 mm in diameter. Other formats are encompassed by the present invention, such as, but not limited to: 6, 12, 24, 48, 96, 384-wells. It is known to the skilled in the arts to adjust well diameter of the assay format (e.g. cell number) to the scope of the relevant cell-based assay. Modifications of the multiwell device to facilitate microscope reading, handling or manipulation of the assay are encompassed by the present invention, as well as modifications to make the multiwell device compatible with any instrument or equipment that may be associated with the use and application of the device, whether for handling, qualitative or quantitative measurement purposes.

Multiwell device is preferably made of polycarbonate, however other materials are encompassed by the present invention, such as but not limited to: glass, acrylic, plexiglass, polystyrene, polypropylene, etc. Modifications of device material with respect to facilitating protein adsorption, or ensuring compatibility with organic or aqueous solutions of the procedure, or other modifications as known to the skilled in the arts, are encompassed in the present invention.

The multiwell device is coated with a thin paint coat, thus creating and delimiting each circular area, in such way that no cross-contamination occurs between samples. As the coat may be of different thickness, the circular areas may be delineated by an edge of different thickness and height, turning the area into a well of different depth.

Figure 5A:
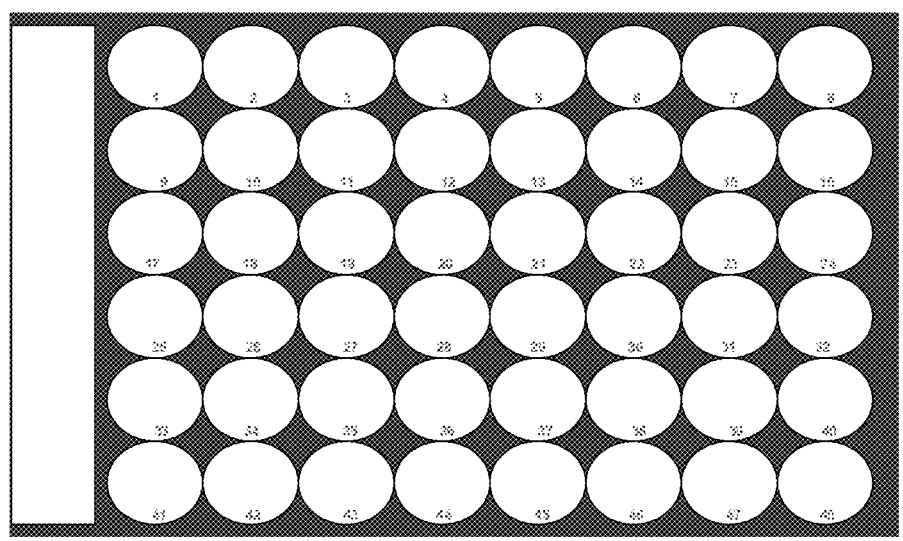
FIGS. 5A-5D: Multiwell device and accessories for manual Pap staining of cervical samples. A. Multiwell Device for sample deposition, staining and evaluation of multiple specimens featuring 48 delimited areas of 13 mm diameter which are numbered for easy tracking. B-C. Stainless steel multiwell device holders with 3 multiwell device capacity. D. Solvent resistant multiwell staining reservoirs, designed for thorough staining in minimal solution volume. Plastic stand holds reservoirs in place.

In a specific embodiment, illustrated in FIG. 5A, the multiwell device consists of a glass plate (130×90×1.2 mm) coated with a hydrophobic PTFE film (Teflon), partitioning the surface into 48 circular areas of 13 mm diameter each, referred to as "wells". The wells are numbered, on the back of the plate, for easy tracking and pre-treated with L-polylysine for optimal cell adhesion. The side of the multiwell device features an area for barcode label attachment. The Teflon film prevents cross contamination between patient samples deposited in the wells. It is also resistant to organic solvents. Insofar, this particular multiwell format is a preferred device for Pap staining of cervical samples as described in Examples 5-7.

The method of the present invention enables the analysis of multiple samples simultaneously. Insofar, it has utility application as a high-throughput format for a variety of cell-based assays, including conventional cytology and cell immunostaining, commonly performed on individual glass slides. It is particularly emphasized herein that the device and methods of the present invention can be applied to cell biology assays and applications thereof, including but not limited to the screening and evaluation of drugs and small molecule compounds, and the study of cellular pathways, as known to the skilled in the art.

In preferred embodiments of the present invention described below, the multiwell device is applied with particular emphasis to cervical detection and screening.

Cervical Samples. For the purpose of the present invention, cervical sample is intended to be any sample directly collected from a patient cervix including cells, tissue or body fluid, using any device, including but not limited to brush, swab, spatula, by scraping or swabbing an area or by using a needle to aspirate bodily fluids. Cervical samples can also be derived from, but not limited to, human fresh or frozen tissues, paraffin embedded tissue, biopsy sample, exfoliated cervical cells, or cervical mucosal samples, or cervicovaginal lavage samples.

Furthermore for the purpose of the present invention, cervical samples comprise cervical cells, in suspension, derived from cervical specimen collected according to liquid-based cytology such as, but not limited to, ThinPrep preparation (Hologic), or SurePath (BD). Indeed, in particular embodiments of the present invention cervical cells derive from ThinPrep aliquots.

Further encompassed in the present invention are cervical cell suspensions using other preservative liquid-based cytology solutions, such as alcohol-based cytology or immunohistochemistry-type solutions, or cervical cells in suspension in non-preservative solutions, such as phosphate buffer saline (PBS). Cervical cells collected by any technique mentioned above or obtained from any solutions mentioned above, and then smeared to a glass slide, including as a cell monolayer, are contemplated in the present invention.

Further encompassed in the present invention are any other biological fluids containing cells that can be evaluated by cytological stain, microscope examination, immunostaining with specific antibody or combination of antibodies. Such biological fluids include but are not limited to: bronchio-alveolar lavages, sputum, gynecological smears, nipple aspirate fluids, urine, etc. In many instances, such biological fluids are associated with the detection of diseases and conditions of specific organ sites, e.g. bronchio-alveolar lavages for asthma, or lung cancer and lung diseases, nipple aspirate fluids for breast cancer, urine sediments after digital rectal examination for prostate cancer, etc. Furthermore encompassed in the present invention are cells derived from, but not limited to, human fresh, frozen tissues, paraffin embedded tissue, biopsy sample, microdissected tumor tissues etc. Therefore, the device and methods of the present invention have utility application in the detection and possible screening of a variety of diseases, beyond cervical and gynecological diseases.

Cytological stains using multiwell device. The methods of the present invention first comprise the use of the multiwell device in conventional cytological staining. Indeed, in a preferred embodiment of the present invention, the application of the multiwell device to the classical hematoxylin staining is demonstrated (Example 1, FIGS. 2A-2D). Cervical cells from a normal Thin Prep patient sample are deposited in one circular area of the multiwell device. Multiple samples can be simultaneously handled, stained and visually evaluated under microscope. Thus the multiwell device has utility application in converting to high throughput format a variety of cell-based assays, including cervical screening.

In this embodiment, the multiwell device has been UV irradiated to enable cell attachment. Alternate methods for cell attachment are known to the skilled in the arts (such as, but not limited to polylysine, crosslinking agents, plastic treatment for cell adsorption, etc.) and are encompassed by the present invention, depending on the material the device is made of.

It is known to the skilled in the arts, that the size of the circular areas on the multiwell must be reasonably compatible with the amount of cells one wants to examine. Thus, depending on the scope of the experiment, whether visualization, detection, or screening, one will chose a sample volume and cell number that can be reasonably accommodated and spread in the well surface of the selected multiwell. For example, a 15 mm diameter well may accommodate about 300,000 cells, which is the number of cells a pathologist might have to screen to achieve a reasonably accurate Pap diagnosis.

After depositing cells on the multiwell, cells are air dried at RT, or alternatively in a 37-40° C. chamber, then rinsed with PBS. Cells are cleared from excess debris, a notorious impairment of cervical Thin Prep smears. In a specific embodiment, hematoxylin staining is performed (Example 1, FIGS. 2A-2D), thus coloring cell nuclei in blue, and visual evaluation of the samples under microscope is performed. The results, as shown in FIGS. 2A-2D, demonstrate that cytological staining can be successfully performed in the high-throughput multiwell device format of the present invention.

Application of multiwell device to cervical cancer screening. The device of the present invention has utility application in high-throughput cervical disease detection and screening.

Because preneoplastic, dysplastic and cancerous human cervical samples are rare, this particular embodiment of the present invention resorts to an experimental condition that mimics a patient sample for cervical cancer screening, by mixing normal cervical cells with cells from a cancer cell line, that are grown together overnight in co-culture (Example 2).

As described in detail in Example 2, cervical cells from a normal patient Thin Prep sample are deposited on a single circular area of the multiwell device, and treated as in Example 1 (i.e. air dried and rinsed with PBS). Subsequently cells from a cancer cell line are layered on each individual circular areas of the multiwell device, and incubated ON at 37° C. to spread and attach. The next day, cells are fixed with 95% ethanol to ensure cancer cell attachment, and hematoxylin stained. Multiple patient cervical samples can be used simultaneously on the multiwell device, and the co-culture may use varying amounts of cancer cells with respect to normal cells.

In the specific embodiments of the present invention the cervical cancer cell line SiHa (a human squamous cervix carcinoma cell line containing integrated HPV16 genome) is used, but any cancer cell line can be used for this purpose. The co-culture of a few cancer cells among normal cervical cells mimics the assay condition of a patient sample for cervical cancer screening, where a few abnormal cells need to be recognized in a field of normal cells.

Microscope evaluation results in the observation of round or elongated cancer cells that have grown amongst normal squamous cervical cells, characterized by their large polygonal shape and the hematoxylin-based blue staining of the nuclei. Because in this example, normal cervical cells and cancer cells are both stained with hematoxylin, they can only be distinguished on the basis of cell morphology alone. The difference in cell shape between cancer cells and normal cervical cells may be observed in FIGS. 3A-3G below. In contrast, in the following embodiment (namely Example 3, FIGS. 3A-3G), normal cervical cells are stained with hematoxylin, while cervical cancer cells are stained with a specific antibody. Therefore, normal cervical cells and cancer cells can be distinguished on the basis of cell morphology and on the basis of a specific immunostaining.

In this specific embodiment hematoxylin staining is performed. However, the present invention encompasses staining of normal and abnormal cells on the multiwell device with any cytological stain, including the Papanicolau stain used in cervical screening. Insofar, the device and method of the present invention finds utility application in cervical disease detection and screening.

In conclusion, this specific embodiment of the present invention confirms that co-culture and hematoxylin staining of a few cancer cells among normal cervical cells enable microscopic evaluation of cell morphology differences, serving as an experimental model of a patient sample for cervical cancer screening.

The co-culture model used in this specific embodiment of the present invention can be applied to cells from any other biological fluids, other than cervical smears and Thin Prep, such as but not limited to: bronchio-alveolar lavages, sputum, nipple aspirate fluid, cerebrospinal fluid, peritoneal fluid, plasma, serum, semen, prostatic fluid, etc. Insofar, the multiwell device can be successfully applied to the examination of such biological fluids that may be associated with detection of diseases and various conditions at various organ sites, extending utility application of the multiwell device to disease and screening beyond gynecological diseases. As mentioned above, other cancer cell lines and tumor cells may be used in conjunction with other biological fluids, so that the present invention encompasses various other models of cancer or disease detection and screening.

Immunostaining of patient cervical samples using multiwell device and commonly used antibodies. In cervical screening, there is a need to improve Pap smear accuracy. Antibody immunostaining represents a more "objective test" than subjective visual reading of cell morphologies.

As used herein the term "antibody" refers to a polyclonal, monoclonal, recombinant antibody, full-size molecule or antibody fragment thereof, including but not limited to Fab, scFv, single chain variable fragment, affibodies, diabodies, and any other antibody fragment retaining the relevant antigenic determinant binding site. The term "antibody" is used interchangeably herein to refer to any of the above species. Thus, antibodies include antibodies produced in vitro as well as antibodies generated in vivo in a mammal capable of immune response. Methods to produce polyclonal, monoclonal, recombinant antibodies and fragments thereof are know to the skilled in the art (Colligan et al, Current Protocols in Immunology, Wiley Intersciences; Kohler et al. Nature 256:495-497, 1975; Phage display of peptides and proteins—A laboratory manual, Kay B. B., Winter J. & McCafferty J., Eds, Academic Press, 1996).

Thus, immunostaining may serve as an adjunct to the morphological interpretation offered by the pathologist. Antibodies against specific biomarkers may assist in the diagnostic interpretation of preneoplastic and dysplastic lesions in cervical cancer screening, by increasing accuracy of histopathology or cytology-based diagnosis.

Therefore in a preferred embodiment of the present invention, immunostaining of multiple cervical samples is simultaneously performed in the multiwell device of the present invention, using commercially available and commonly used antibodies (Example 3, FIGS. 3A-3G). It is understood by those skilled in the arts, that the use of antibodies against antigens known to have different cell localizations, i.e. nucleus, cytoplasm or membrane, may further assist pathologist diagnosis based on cytology or histology alone.

This embodiment resorts to the experimental conditions established in Example 2, relating to a mixture of normal cervical cells and cancer cells mimicking a patient sample for cervical cancer screening, as preneoplastic, dysplastic and cancerous cervical samples are rare.

The mixture of cells is treated with 95% ethanol to ensure cell adherence to the multiwell surface during the procedure, however other protocols known in the arts ensuring this purpose are encompassed by the present invention.

In this specific embodiment, the multiwell device enables the simultaneous assay of multiple samples comprising a constant number of normal cervical cells, and an increasing number of cancer cells. In this example, cervical cancer cell line SiHa was used, yet the present invention encompasses any preneoplastic, or neoplastic cell line, or tumor cell. Cell mixtures, with varying ratios of cancer to normal cells, are made in triplicate to test for reproducibility, and treated for immunostaining. Multiple samples from the same patient may also be prepared if different antibodies with different staining pattern (nuclear, cytoplasmic or membrane) are used in order to better confirm diagnosis.

In the preferred embodiment of the present invention, the primary antibody used is a monoclonal antibody against p16(INK4a). However, the method of the present invention encompasses any antibody, as defined above (e.g. polyclonal, monoclonal, cell culture supernatant, purified or not, recombinant, etc.) and variant thereof, against any antigen with any cell localization.

In the example detailed herein, the immunostaining procedure comprises the use of anti-mouse IgG biotinylated secondary antibody followed by streptavidin linked to horseradish peroxidase, finally followed by the addition of a precipitating DAB substrate. After hematoxylin counterstain to color cell nuclei in blue, the multiwell device is observed under microscope.

Other immunostain procedures known in the field are encompassed by the present invention. For example, protocols based on different labeling and detection systems, such as alkaline-phosphatase, biotin-streptavidine, or fluorophores can also be successfully performed within the scope of the present invention. Furthermore, while cervical cells must undergo a pre-treatment to inactivate endogenous peroxidase if peroxidase-based staining is used, said pre-treatment is not necessary when using fluorescence-based imaging system, and the protocol is modified accordingly.

Alternate modifications known to the skilled in the art are encompassed by the present invention, such as but not limited to the following: any method for making antigens more accessible to antibody binding may be used in the practice of the invention, including the antigen retrieval methods known in the art, alternate protocols of substrate selection and staining, alternate methods of blocking endogenous biotin, or non-specific binding (see also below).

According to the method of the present invention, and as shown in FIGS. 3A-3G, the multiwell device of the present invention can be used to discriminate a few cancer cells among normal cells in a mixed population, in an experimental condition mimicking a cervical specimen for Pap screening. Indeed the cervical cancer cells appear stained in brown (DAB) by the anti-p16(INK4a) antibody in a field of normal squamous cervical cells, characterized by their polygonal shape and the hematoxylin stained blue nuclei.

It is emphasized herein that while the method of the present invention is exemplified using antibodies against p16(INK4a), the use of other antibodies against other biomarkers that are overexpressed or differentially expressed in dysplastic, preneoplastic or malignant cervical cells, or the use of antibodies against Ki-67, HPV, and any other infectious disease of the cervix, or the use of any other antibody reacting with cervical cells in normal, disease or healthy status, is encompassed by the present invention.

In conclusion, the method of the present invention relies on an objective antigen-antibody interaction to identify malignant cells in the patient specimen. Insofar, the device and methods of the present invention have utility application as potential improvement to Pap smear accuracy, and as a novel immuno-cytology high-throughput cervical screening.

Cell immunostaining of patient cervical samples using ELISA-type format. A further method of the present invention relates to an immunostaining procedure based on a cell suspension derived from a human sample, and an antibody (or combination of antibodies) in a multi-well ELISA-type format.

When the cell suspension is derived from a cervical sample, and the antibody or combination of antibodies is capable to detect cervical dysplasia, preneoplastic or neoplastic lesions or modifications in a cervical specimen, then the method of the present invention has utility application in cervical cancer detection and screening.

Furthermore, as discussed above, depending on the cell suspension used and on the antibody or combination of antibodies used, then the method of the present invention has also utility application in the detection and screening of other conditions and diseases, beyond gynecological diseases, including cancer at different organ sites.

In a preferred embodiment of the present invention, the cell immunostaining method of the present invention using an ELISA-type format, is applied to detect cancer cells in multiple cervical samples simultaneously (Example 4, Table 1).

In this preferred embodiment, the concept of "multiwell" device format, which has been extensively described so far in the present invention, is extended to the common ELISA-type format ("multi-well"), such as a 96-well plate or equivalent. Plates featuring different number of wells per plate can be envisioned, including but not limited to 6, 12, 24, 48, 96, 384-well plates, allowing for cost effective, user-friendly, and small-scale to high-throughput format, as deemed appropriate, and are all encompassed in the present invention. Furthermore, it is emphasized herein that while the 96-well format might be the most common and user-friendly high-throughput format, other well numbers and sizes may be more compatible with the required number of cells necessary for a cervical screening, as up to 300,000 cells might have to be evaluated to provide for accurate diagnosis. Indeed, it is known to the skilled in the arts to adjust well diameter of the assay format (e.g. cell number) to the scope of the relevant cell-based assay.

While a major application of the present invention is high-throughput screening, the present invention also encompasses application of this cell suspension immunostaining assay in a one-sample version, similarly to fluocytometry assays.

Note that, while the multiwell device of the present invention described above involves a mixture of adherent cells, the multi-well ELISA-type format may involve a mixture of adherent cells, as well as a mixture of cells in suspension. Cells made adherent via different methods, including alcohol fixation or air drying, may be accommodated in a variety of well-plates, while cells in suspension may preferably be treated in round-bottom plates, as they must be centrifuged at each step of the procedure. Note that, as described further below, when dealing with cells in suspension, each step of the procedure is followed by a gentle centrifugation step to ensure cells are collected at the bottom of the well, as detailed in Example 4.

The immunostaining follows the principles of Example 3 (FIGS. 3A-3G), except that by using a specific number of cancer cells in the mixture, antigen-antibody reactivity can be quantified by colorimetric reading, rather than by a semi-quantitative visual reading based on microscope examination.

The present invention encompasses any modification of a multi-well ELISA-type plate, pertaining to the format, well number and size, and material of the plate support. Furthermore encompassed in the present invention are modifications of the support as deemed necessary to be compatible with or to facilitate microscope reading, handling and manipulation, microplate readers handling and manipulation, and any other instrument or equipment that may be associated to the use and application of the present invention whether for handling, or for qualitatively or quantitatively measurement purposes. Furthermore the present invention encompasses any modification to develop manual, semi-automated, and fully automated versions of the device and methods of the present invention. Automation procedures will differ depending on whether the assay resorts to adherent cells or cells in suspension, and all modifications are encompassed in the present invention.

In this preferred embodiment of the present invention, a constant amount of cervical cells from a normal patient cervical sample (Thin Prep) is deposited in each well of a multi-well ELISA-type format with an increasing number of SiHa cervical cancer cells, in a co-culture experiment mimicking a patient sample for cervical cancer screening, as described in Example 2. Mixtures are prepared in duplicate or triplicate to allow for quantification. Cells are treated with H2O2 in view of peroxidase inactivation prior to antibody staining, if a peroxidase-based staining method is used. Then immunostaining with specific antibodies is performed.

Primary antibody used herein for the purpose of this example is anti-p16(INK4a), followed by biotin-conjugated secondary antibody, and by peroxidase-conjugated streptavidine. Antigen-antibody complexes are visualized by addition of a soluble substrate, such as, but not limited to tetra-methyl-benzidine (TMB). Immunoreactivity is scored by measuring the optical density (OD) of the colorimetric reaction via a plate reader at the appropriate wavelength. Other immunodetection systems are encompassed by the present invention. The results of such experiment are reported in Table 1 and show that immunoreactivity, as measured by OD reading, increases relatively to the number of cancer cells in the well. Duplicate samples indicate that the experiment is reproducible.

The method of the present invention offers some advantages over the conventional ELISA type assay. Indeed, in the conventional ELISA procedure, cell protein extracts are coating the multi-well plate, instead of intact cells. Therefore, the biomarker must be soluble to be detected in an ELISA assay. On the contrary, whether soluble or not, the biomarker will be detected in an intact cell. This advantage is particularly important, as several publications have pointed to the poor quality of protein extracts derived from cervical cells (Ding, 2008; Ge Y et al., Proteomic analysis of high-grade dysplastic cervical cells obtained from ThinPrep slides using laser capture microdissection and mass spectrometry, J Proteome Res 6:4256-4268, 2007). The poor protein yield obtained from cervical cell extracts may affect the accuracy and reproducibility necessary to a conventional ELISA assay.

It is known in the art, that current cervical screening has significant intra- and inter-observer variability. In a previous embodiment of the present invention, i.e. cell immunostaining in the multiwell device format, we have shown that the use of antibodies provides increased accuracy over evaluation of cell morphology alone. In this specific embodiment, i.e. cell immunostaining using a multi-well ELISA-type format, we further show that immunoreactivity can be quantitated particularly through a colorimetric reading, and that the assay is reproducible.

In the context of cervical screening, where conventional cervical cytopathology requires significant human resources and equipment, colorimetric reading of cervical cell immunostaining is a further utility application of the present invention. Colorimetric reading clearly facilitates sample evaluation, eventually offering an alternative to pathologist evaluation.

In conclusion, we demonstrate that the utility applications of the present invention are: i) simultaneous handling of multiple samples, and ii) immunostaining, representing an improvement over conventional Pap smear screening as well as current ThinPrep cervical screening.

Kits for practicing the methods of the invention are further provided.

Automation. As known to those skilled in the arts, a device can be used and high throughput methods can be practiced in a manual, semi-automated or fully automated format. Classical cytological stains, including the Pap staining for cervical disease screening, as well as immunohistochemistry procedures as applied to multiple slides, have been since long developed into automated equipment and procedures allowing the handling of a large number of multiple samples per hour.

Are encompassed in the present invention, systems, apparatus, methods and modifications thereof, allowing for the automatic control and scheduling of all the tasks necessary to the performance of the automated procedures involving the multiwell device, such as but not limited to: sample deposition, air blowing, washing, staining in multiple baths at specific intervals, adding or removing reagent bottles or fluid containers, mixing reagents, applying reagents to the device, introducing new solid support (i.e. multiwell device) with additional samples, increasing throughput, moving solid support along the procedures, capturing images of the device, measuring colorimetric reactions, etc.

Partial or complete automation of the processes described herein are encompassed by the present invention.

Figure 4:
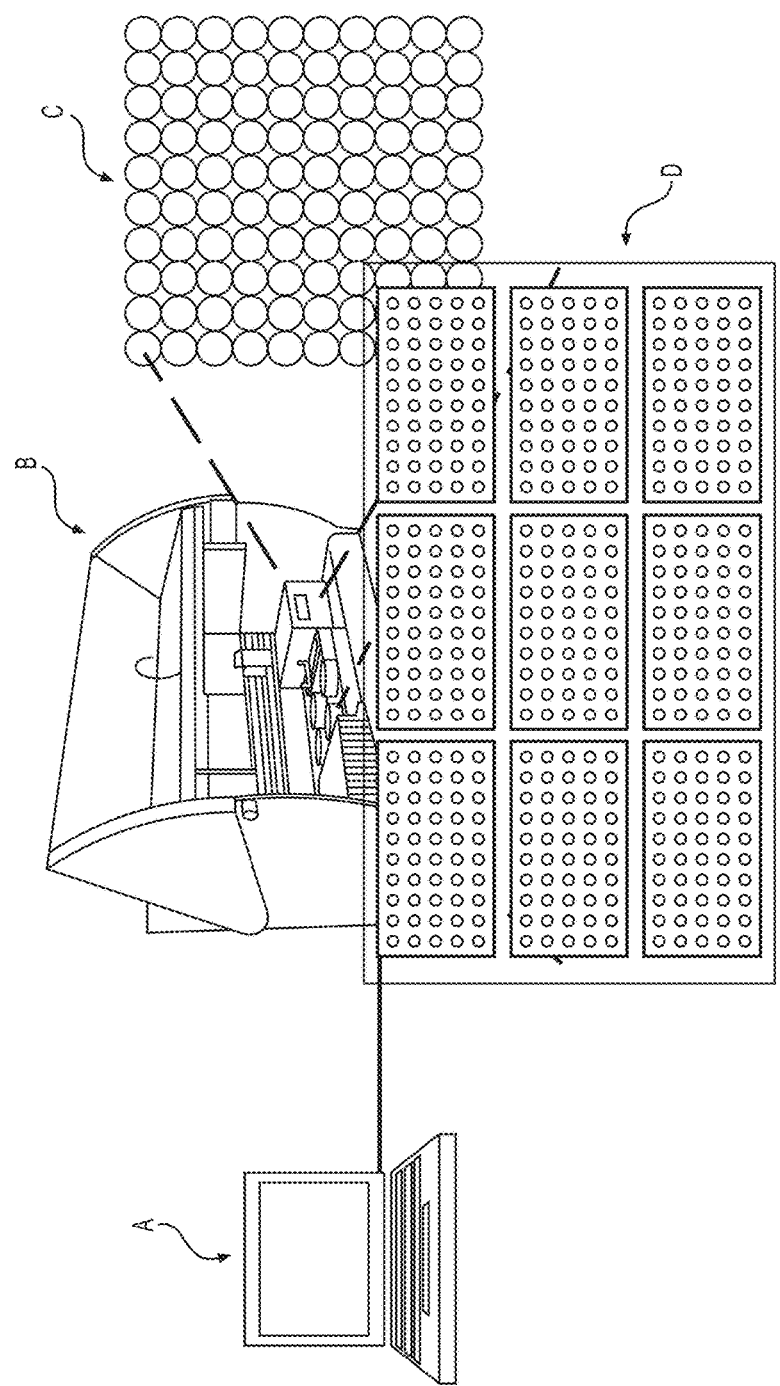
FIG. 4: System automation. Schematic illustration of a simplified example of the automation of the system of the present invention, comprising: a computer system (which can also be incorporated in the robot) featuring a software application controlling the robot and all the processes (A), and a robotic device where all the sampling, staining and immunostaining processes occur (B). The latter also includes a rack (C) where patient cervical samples are held, and a platform holding the multiwell devices (D). In this specific example the platform holds 6 multiwell plates of 50 samples each, although other designs are contemplated by the present invention. The robot provides sample vortexing, pipetting and deposition on the multiwell device, as well as plate moving capability. Multiwell plates are then transferred to an automated staining system, which is either incorporated within the sampling robot, or separated.

FIG. 4 provides a schematic illustration of the automation of the present invention. A simplified example of such automated equipment would comprise: a computer system (which can also be incorporated in the robot) featuring a software application controlling the robot and all the processes (A), and a robotic device where all the sampling, staining and immunostaining processes occur (B). The latter would comprise a rack (C) where patient cervical samples are held, and a platform holding the multiwell devices (D). In this specific example, the platform may hold up to 6 multiwell plates of 50 samples each, although other designs with different sample numbers are contemplated by the present invention, as specified above. The robot would provide vortexing and pipetting capability, including sample deposition on the multiwell device, and plate moving capability. Multiwell plates are then transferred to an automated staining system, which may be either incorporated within the sampling robot or separated. Similarly, a plate reader may or may not incorporated in the robot (B).

Manual cervical cytology in multiwell device. The present invention encompasses staining of normal and abnormal cells on the multiwell device with any cytological stain, including the Papanicolau stain used in cervical cytology screening. In fact, the multiwell device is particularly designed for the simultaneous processing of multiple cervical samples, thus increasing assay output with respect to conventional Pap (CP) staining, which is performed on one single slide per patient. In this respect, the multiwell device is well suited for clinical settings lacking access to automated equipment and procedures, as it enables manual high throughput processing and staining of samples, while keeping affordable the cervical disease screening process.

In a preferred embodiment we describe a simple procedure to enrich cervical samples for manual Pap staining on the multiwell device (Example 5). Patient specimens were collected in conical tubes containing cytology preservative solution. Cells were allowed to settle thus enriching the sample preparation by a simple gravity sedimentation step. Conical bottom tubes facilitated cell collection, particularly in scant samples. At this stage, sample cellularity was evaluated based on the volume of the wet cell sediment. Hence 50-100 µl of each cell sediment, depending on its volume (i.e. the larger the cell sediment volume, the smaller the cell sediment withdrawn), were removed from the bottom of the specimen tube, and manually deposited onto a single well of the multiwell device, one patient sample per circular area. This semi-quantitative method allowed adequate representation of most samples, including low cellularity ones.

Figure 5B:
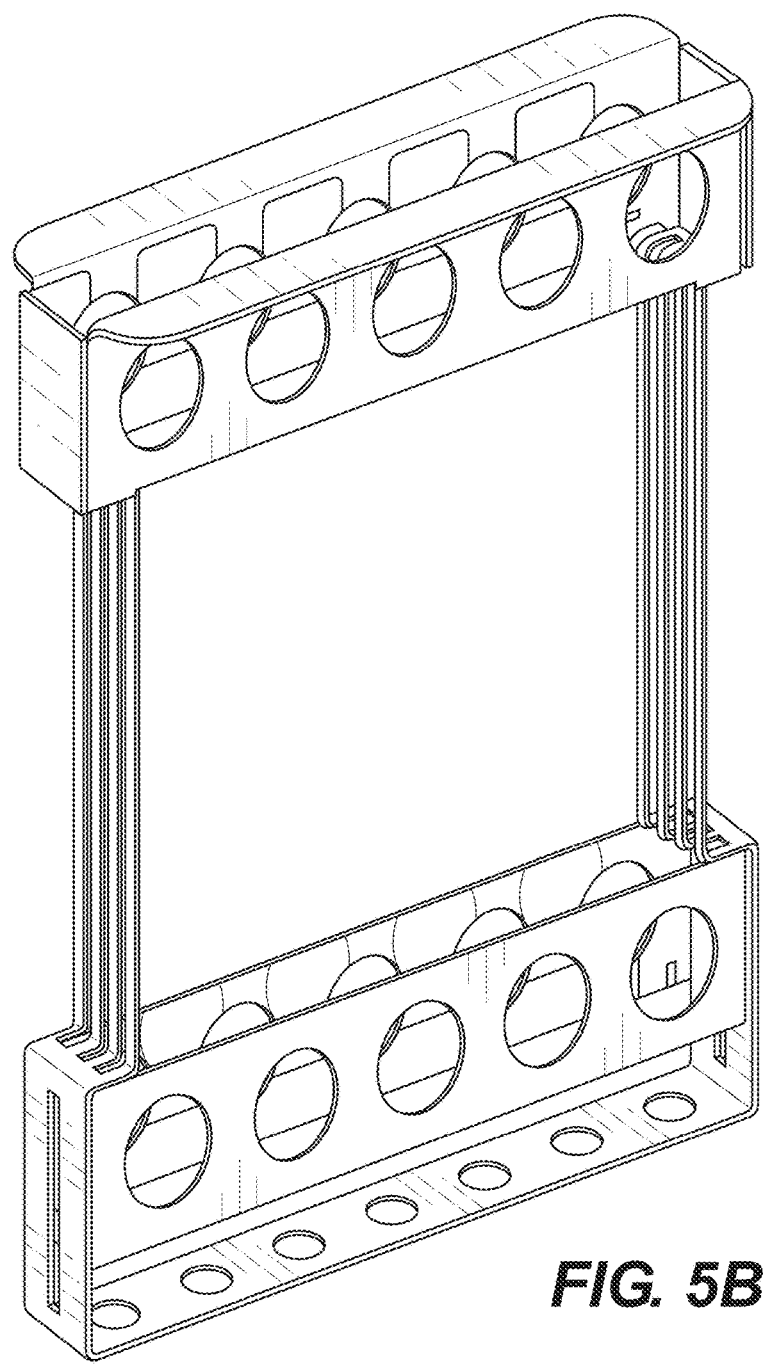
Figure 5C:
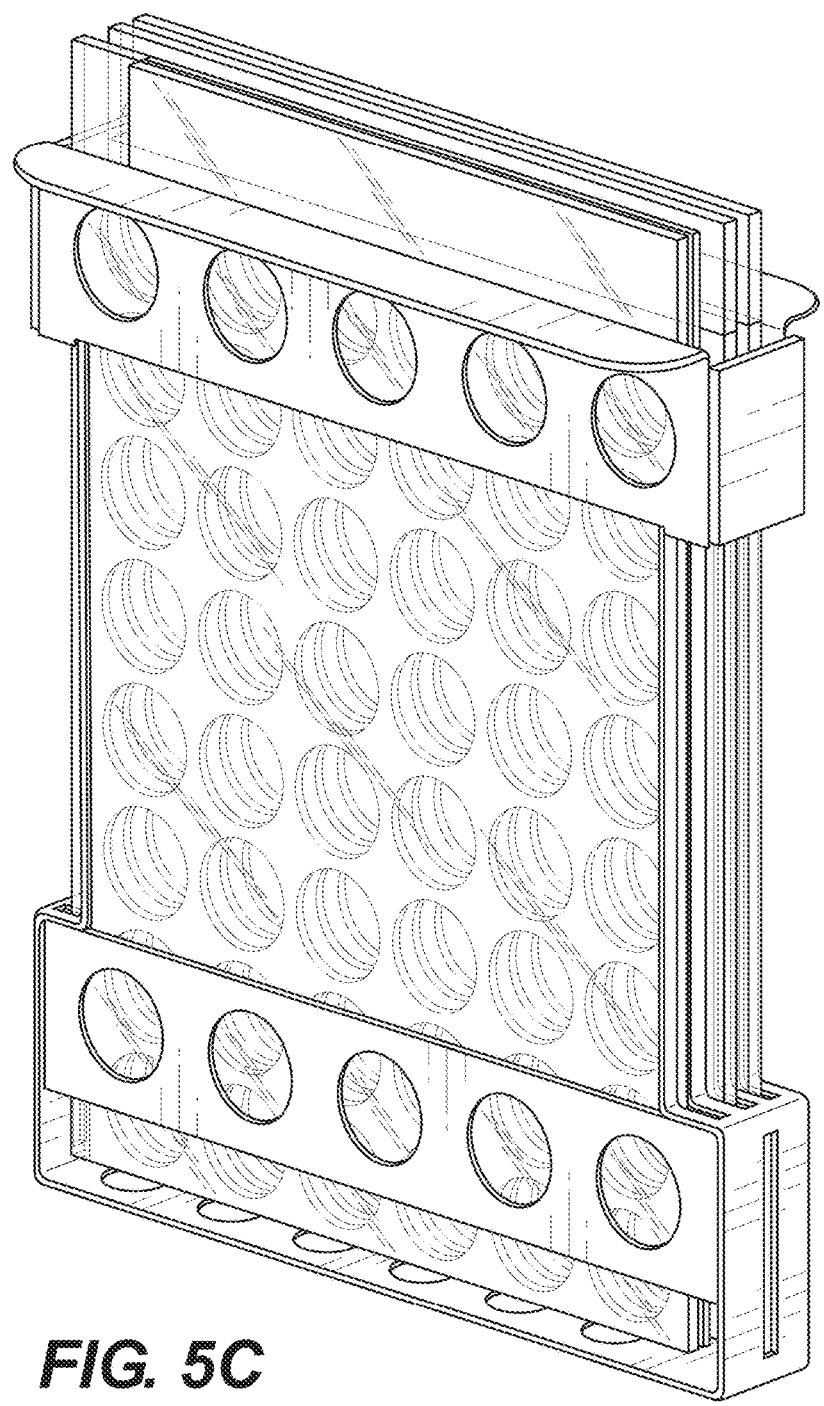
Figure 5D:
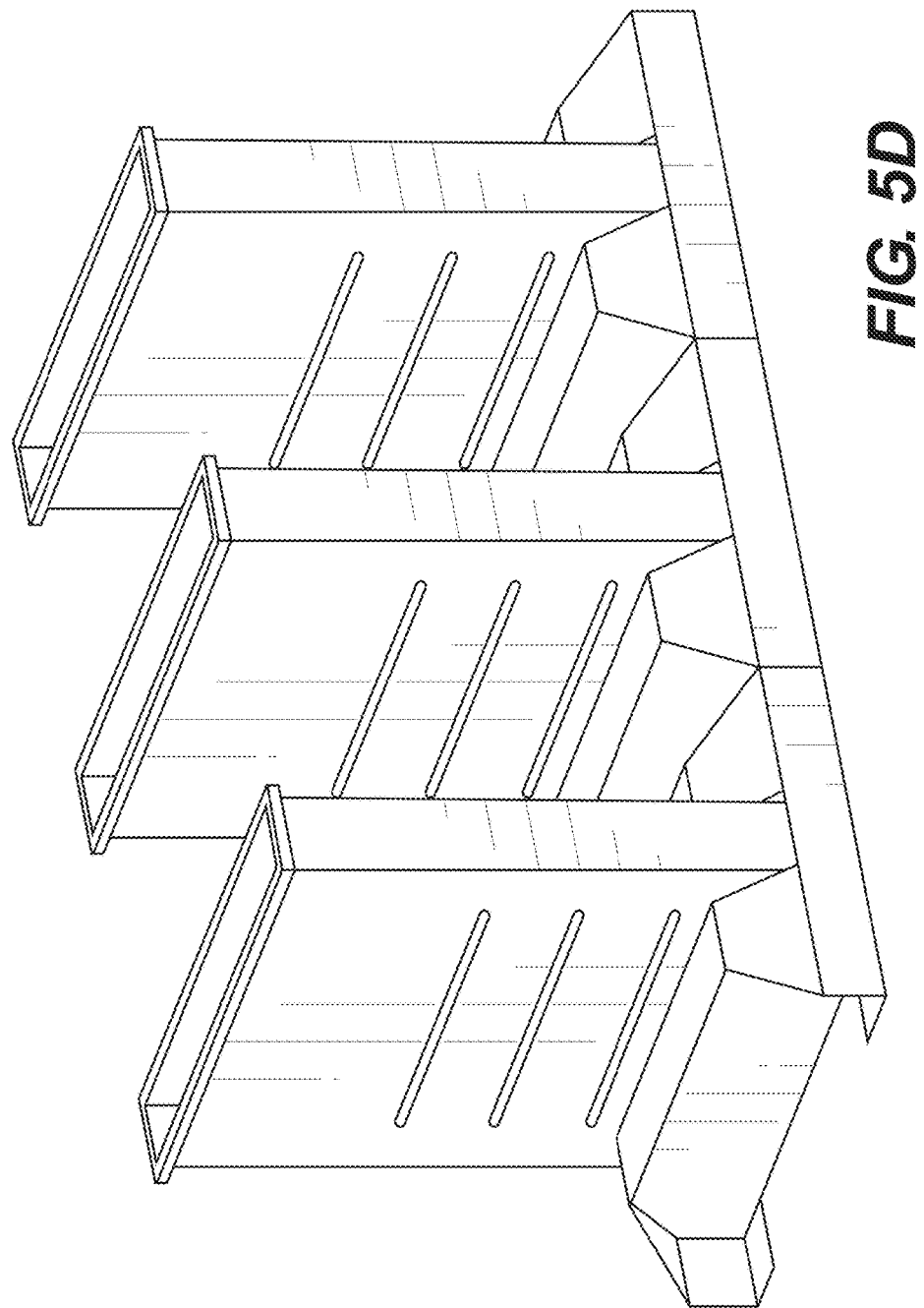

After sample deposition, the multiwell was allowed to air dry prior to manual Pap staining (Example 6). Accessories to facilitate manual staining and increase its throughput are encompassed by the present invention, including but not limited to the ones illustrated in FIGS. 5B-D: stainless steel multiwell device holders with multiple capacity, solvent resistant multiwell staining reservoirs for thorough staining in minimal solution volume, and reservoir stands. The processing time for preparing, layering, and simultaneously staining 48 samples on the multiwell device was approximately 1 hr 15 min. The multiwell device, coupled with the sample enrichment process, offers a novel low-cost and rapid method of manual liquid-based cytology (LBC).

Dual cytology. In another preferred embodiment, we compared the performance of multiwell cervical cytology to conventional Pap smear (CP) in a dual cytology pilot experiment involving 173 patients (Example 7). The multiwell procedure yielded a lower number of unsatisfactory samples than the CP method. In the CP method 18 samples were found inadequate versus 10 samples in the multiwell method. Ultimately, of the 173 samples, 155 in the CP method (90%) and 168 in the multiwell methods (97%) were found satisfactory for evaluation, a difference that was found statistically significant ($p<0.05$). In any LBC method, cell density typically varies depending on patient specimen, because of the variability inherent to sample collection. However the multiwell sample processing method reduces the number of inadequate samples, due to too low or too high cellularity by simply adjusting the volume of the wet cell sediment withdrawn from the specimen collection tube, as described in more details in Example 5. The multiwell offers the flexibility to re-examine a case by adjusting sample cellularity if sample is found inadequate at first analysis. The multiwell procedure thus reduces sample loss and the requirement for patient recall.

The dual cytology pilot experiment further demonstrated that the multiwell method yielded significantly cleaner and easier to evaluate preparations than the CP method. The presence of mucus and debris was evident in most of the CP samples (89%), while the multiwell processing eliminated mucus and debris in the vast majority of the samples (98%). Evidence of red cell lysis was detectable in 7% and 15% of CP and multiwell samples respectively. Therefore, the multiwell procedure significantly reduced the presence of mucus and debris ($p<0.01$), and enhanced red cell lysis ($p<0.05\%$) thus leading to samples less obscured by cell clumps and whole red blood cells. The two methods were comparable based on other morphological criteria examined.

Finally the diagnostic results between CP and multiwell procedure were compared. Of the 155 matched paired samples, 141 were assigned the same diagnosis, thus yielding 91% agreement betwee.......n the two methods (Kappa=0.83, 95% CI 0.75-0.92]. Cytologic evaluation of single CP and multiwell slides identified 81 normal, and 60 dysplasia cases counting 48 ASCUS, 8 LSIL(-IN1), and 4 HSIL, comprising 3 CIN2 and 1 CIN-3. CIN1-3 cases were confirmed by histologic examination of corresponding biopsies. The 14 remaining paired samples were assigned different diagnoses between the two methods, with 9 cases assessed as ASCUS in the multiwell versus normal in the CP method, and 5 cases reported as normal in the multiwell versus ASCUS in the CP method. However, because the 9% discordant cases were all within one degree of change, and thus were not considered major diagnostic discrepancies, an even stronger agreement between the two methods was found by weighted Kappa statistics (0.87, 95% CI 0.80-0.94). Overall, the dual cytology study demonstrates the feasibility and performance of manual Pap staining on the multiwell.

While an embodiment of the present invention as been shown and described, various modifications may be made without departing from the scope of the present invention, and all such modifications and equivalents are intended to be covered.

EXAMPLES

The following abbreviations are used throughout. ddH2O: double distilled water; hr:hour; min:minutes; sec:seconds; ON:overnight, rpm:rotation per minutes; RT:room temperature.

Example 1

Hematoxylin staining of patient cervical samples using multiwell device. A fraction of an individual Thin Prep sample (i.e. 250 µl volume, approximately 50-100,000 cells) is layered on a single circular area of the multiwell device. Multiple samples can thus be handled and evaluated simultaneously. The device has been previously UV irradiated to enable cell attachment. However, alternate methods for cell attachment can be utilized depending on the material the device is made of. Samples are air dried either at RT or in a 37-40° C. chamber, then rinsed with PBS. Cleared from excess cell debris, cells are ready for any cytological stain.

In this specific embodiment, hematoxylin staining is performed. For hematoxylin staining, multiwell device is rinsed with ddH2O, and covered with a few drops of weak Mayer's hematoxylin solution for 1-2 min. Multiwell device is rinsed twice with tap H2O or bluing solution (Scott's tap water, or sodium or lithium carbonate solution to ensure alkaline pH) to stain cell nuclei in blue, and once with ddH2O. Mounting medium may be applied as appropriate for slide preservation. Alternatively, multiwell device is immediately observed under microscope using different magnifications either as is or air dried (FIGS. 2A-2D).

Example 2

Co-culture and hematoxylin staining of patient cervical cells and cancer cells in multiwell device, in an assay condition mimicking Pap smear screening. First, 250 µl of an individual Thin Prep sample, previously diagnosed as normal, is layered on a single circular area of the multiwell device. Multiple samples can thus be handled and evaluated simultaneously. Samples are air dried then rinsed with PBS, and stained with hematoxylin, as described in Example 1. The multiwell is rinsed with 95% ethanol prior to the addition of cancer cells.

The cervical cancer cell line SiHa (ATCC # HTB-35), a human squamous cervix carcinoma cell line, reported to contain one to two copies per cell of integrated HPV16 genome, is used in the co-culture experiment together with cervical cells from Thin Prep samples. Cell line is cultured according to ATCC or provider's recommendations, trypsinized and counted according to standard procedures. A few SiHa cells are deposited on each individual circular areas of the multiwell device, and incubated several hours to ON at 37° C. to spread and attach. The next day, cancer cells are fixed with 95% ethanol, and hematoxylin stained, as described above. Alternatively, cervical cells and cancer cells are deposited in two separate steps, and a single hematoxylin staining is performed at the end. Microscope evaluation results in the observation of elongated cancer cells that have grown amongst large polygonal squamous normal cervical cells, which are visualized by their nuclei blue staining. In this example, cancer and normal cervical cells are distinguished on the basis of cell morphology alone. These results confirm co-culture of normal cervical cells and cancer cells as an experimental model of Pap smear screening.

Example 3

Immunostaining of patient cervical sample using multiwell device and commonly used monoclonal antibodies. This example describes how immunostaining can be performed in the multiwell device using commercially available and commonly used monoclonal antibodies. This example thus further demonstrates the utility of immunostaining as an adjunct to microscopic evaluation of cell morphologies in cervical screening.

Because preneoplastic, dysplastic and cancerous Thin Prep samples are rare, we resorted to an experimental condition mimicking a patient sample for cervical cancer screening, ie. mixing normal cervical cells with cells from a cancer cell line that are grown ON in co-culture, as described in Example 2. In this experimental model, a constant amount of normal patient cervical cells derived from a previously diagnosed normal Thin Prep (250 µl) is layered in each circular area of the multiwell device, air dried at RT or in a 37-40° C. chamber then rinsed with PBS. Subsequently, some cancer cells (i.e. enough to be visualized in a field for the purpose of the example) are layered, in triplicate, and grown ON at 37° C. The next day, cells are fixed with 95% ethanol, however, instead of proceeding with hematoxylin staining as in Example 2 above, the multiwell device is treated for immunostaining. In this example, SiHa cervical cancer cells are used and stained with monoclonal antibodies against p16(INK4a), using an appropriate volume of a 1 µg/ml solution in PBE (i.e. PBS with 1% BSA, 1mM EDTA, 1.5 mM NaN3, pH7.4), enough to cover cells. Note that cells must be treated with H2O2 to inactivate endogenous peroxidase, as described in detail in Example 4 below, if a peroxidase-based detection system is used. The primary antibody is incubated for 1 hr at 37° C. Then, for detection, an anti-mouse IgG biotinylated secondary antibody (Jackson Lab) diluted to 1 µg/ml in PBE is added to each area of the multiwell device, and incubated for 30 min at 37° C. Secondary antibody is followed by Streptavidin linked to horseradish peroxidase (Jackson Lab) diluted to 1 µg/ml in PBE without azide, and incubated for 15 min at RT.

The reaction is developed by the addition of a freshly prepared peroxidase substrate, such as DAB (3-3'diaminobenzidine tetrahydrochloride substrate at 5 mg/ml) or AEC (3-amino-9-ethylcarbazole substrate) followed by incubation at RT. Color development is checked under the microscope and the reaction stopped with PBS containing 0.05% azide. Hematoxylin counterstaining is performed to color cell nuclei in blue, and the multiwell device is observed under microscope. Necessary controls in this experiment include: a) normal cervical cells only; b) cervical cancer cells only; c) a mix of cervical cells and cancer cells, no primary antibody; d) cancer cells only stained with anti-p16 (INK4a) antibody.

FIGS. 3A-3G show that specific immunostaining enables further discrimination of a few cancer cells in a background of normal cervical cells, in an experimental condition mimicking a Pap smear specimen, in addition to the observation of cell morphology differences alone.

Example 4

Immunostaining of patient cervical sample and cancer cells in solution using ELISA-type format and commonly used monoclonal antibodies. In this example, the concept of multiwell device format is extended to the commonly known ELISA-type format, such as a 96-well flat-bottom plate or equivalent. In fact, plates featuring various numbers of wells can be envisioned, as deemed appropriate, namely 6, 12, 24, 48, 96, or 384-well plates, allowing for cost effective, user-friendly, and small-scale to high-throughput format, as needed. Furthermore, it is emphasized herein that while the 96-well format might be the most common and user-friendly high-throughput format, other numbers and sizes of wells may be more compatible with the required number of cells necessary for a cervical screening, as up to 300,000 cells might have to be evaluated to provide for accurate diagnosis.

Furthermore, while the multiwell device assay involves a mixture of adherent cells, the 96-well plate format may involve a mixture of adherent cells, as well as a mixture of cells in suspension. Note that when dealing with cells in suspension, each step of the procedure is followed by a gentle centrifugation step to ensure cells are collected at the bottom of the well.

Finally, in this example the immunostaining follows the principles of Example 3 (FIGS. 3A-3G), except that by using a specific number of cancer cells in the mixture, antigen-antibody reactivity can be quantified by colorimetric reading, rather than by a semi-quantitative visual reading based on microscope examination.

In this embodiment, a mixture of normal cervical cells and cervical cancer cells is used, as previously described in Examples 2 and 3 (FIGS. 3A-3G), an experimental condition mimicking a patient sample for cervical cancer screening. First, a constant amount of normal patient cervical cells derived from a previously diagnosed normal Thin Prep (250 µl volume; approximately 50-100,000 cells) is deposited in each well of a multi-well plate, i.e. a 96-well plate for the sake of this example. Multi-well plates are preferably tissue culture treated for cell adhesion, unless the protocol is used in the cell suspension mode (see below).

Thin Prep cells must be treated to inactivate endogenous peroxidase. Plates containing cervical cell samples are treated with an appropriate volume of 1% hydrogen peroxide solution diluted in PBS (H2O2; 100 to 300 μl/well depending on well size) for 30 min at RT with gentle 400 rpm shaking. After peroxidase inactivation, cells are rinsed three times with PBS, centrifuged and supernatant is discarded.

At this point, cells are air dried at RT, if they are subsequently treated as adherent cells. The multiwell is rinsed with 95% ethanol prior to the addition of cancer cells. Alternatively, they are gently centrifuged at each step, if treated as cells in suspension. An increasing number of SiHa cervical cancer cells (200 to 1,200 cancer cells/well) is layered, in duplicate, and grown ON at 37° C. The next day, cells are fixed with 95% ethanol, if cervical cells had been previously air dried. Alternatively, they are centrifuged if cervical cells had been previously centrifuged.

This example can also be successfully executed by layering the same volume of cervical cells with the given number of cancer cells, followed by peroxidase inactivation treatment. Then, cells are either air dried and washed with PBS, or they are centrifuged, depending on the procedure (i.e. fixed cells versus cells in suspension) that was elected.

To block endogenous biotin cells are incubated for 30 min at RT in a Streptavidin solution in PBE without azide (100 μg/ml), followed by a PBST rinse. Then cells are further incubated with a biotin solution (500 μg/ml) in PBE (PBS with 1% BSA, 1mM EDTA, 1.5 mM NaN3, pH7.4) followed by three PBST rinses, then cells are centrifuged and supernatant is discarded.

After layering the cell mixture, and performing the peroxidase inactivation and the endogenous biotin block, finally the plate is treated for immunostaining. All incubation steps are 30 min long and performed at RT under 400 rpm shaking for the rest of the procedure.

Plates are incubated with relevant anti-p16(INK4a) primary antibody (50 μl/well for a 96 well plate, or enough to cover cells, of an appropriate dilution in PBE buffer for 30 min, at RT). Cells are washed three times with PBST to remove unbound primary antibody (specifically, wells are filled with buffer, plates are centrifuged 10 min at 1500 rpm, and supernatant is discarded).

A biotin-conjugated secondary antibody (for the purpose of the invention a biotin conjugated goat anti mouse IgG) is then added to each well (50 μl of a 1 μg/ml solution of the biotinylated secondary antibody in PBE buffer) and cells are incubated as described above (30 min, RT, 400 rpm). Cells are washed three times with PBST to remove excess secondary antibody as described above. Cells are spun down for 10 min at 1500 rpm, and the supernatant is carefully aspirated, preferably with vacuum.

Peroxidase-conjugated streptavidine is added to each well (50 μl of a 1 μg/ml dilution in PBE buffer without azide) and cells are incubated 15 min at RT with 400 rpm shaking, as described above. After one wash with PBST and two washes with PBS, antigen-antibody complexes are visualized by the addition of 50 μl of TMB substrate solution to each well, followed by incubation for 10-40 min at RT and 400 rpm shaking. Blue color will appear within 10 minutes with varying strength based on the amount of cells per well and on antigen concentration. The reaction is stopped by filling wells with H2SO4, turning the blue solution to a yellow color read at 450 nm. Immunoreactivity is scored using a colorimetric ELISA plate reader. Alternatively, the solution is preferably transferred to a fresh plate and immunoreactivity read.

Example 5

Multiwell sample processing and enrichment. To process cervical specimens through the multiwell, barcoded patient collection tubes containing cervical samples in cytology preservative solution, were first linked through a log to a given numbered well of a barcoded multiwell plate. Then, samples were vortexed and allowed to settle for 5 minutes. Finally, for each sample, 50-100 μl, depending on the volume of sedimented cells (with 100 μl withdrawn from small sediments, 75 μl from medium, and 50 μl from large sediments), were withdrawn from the bottom of the tube, and spread onto a single well of the multiwell device, in order to cover the entire circular surface of the well. The multiwell was allowed to dry flat for 15 min at room temperature prior to staining.

Example 6

Pap Stain of cervical samples using the multiwell device. After sample deposition, multiwell plates were stained in jars of appropriate size, using enough staining solution at each step to evenly and thoroughly cover their surface. In order to achieve higher throughput, multiwell holders were designed to hold 3 multiwell plates at a time, and the metal holders were inserted into staining reservoirs to be stained effectively using limited volume of staining solutions (FIGS. 5A-D). Papanicolau staining solutions and procedure were as follows: dH2O: 10 min; Nuclear Stain: 5 min; dH2O: 10 sec; Rinse Solution: 1 min; dH2O: 30 sec; Bluing Solution: 30 sec; dH2O: 30 sec; 50% alcohol: 30 sec; 95% alcohol: 30 sec; Orange G: 2 min; 95% alcohol: 15 sec; 95% alcohol: 15 sec; EA Solution: 4 min; 95% alcohol: 1 min; 95% alcohol: 1 min; 100% alcohol: 30 sec; 100% alcohol: 30 sec: 100% alcohol: 30 sec; xylene: 30 sec: xylene: 1 min; xylene: 3 min. Individual wells of each multiwell plate were covered with Permount mounting medium, coverslipped, and evaluated by a pathologist.

Example 7

Comparison between multiwell cervical cytology and conventional Pap. Dual cytology was performed to compare the multiwell cervical cytology method to the conventional Pap (CP). The split sample method was used to collect cervical specimens from 173 women, 23 to 45 years old, who provided signed informed consent. Using a cytobrush, one sample per patient was collected, both from the endocervix and the exocervix to ensure adequate representation of cervical cells in the specimen. One side of the brush was applied on a single slide and smeared to produce a CP slide, then the brush was dipped into a 5 ml polycarbonate conical self-standing transport screw-cap tube, containing 4 ml of cytology preservative solution and swirled to thoroughly disperse cells for multiwell based LBC. The slide was immediately fixed with Fisherbrand CytoPrep Fixative spray, and Pap stained, while the vial was processed according to the multiwell procedure described in Examples 5 and 6. Paired specimens were numbered 1-173. Evaluation by pathologist/cytopathologist included monolayer cell adhesion, cellularity, background clarity, preservation of cellular morphology, red cell lysis, and elimination of mucus and debris. Samples were scored as unsatisfactory, borderline, acceptable, good and excellent, and diagnosed according to the Bethesda classification system (Solomon D, Davey D, Kurman R et al. The 2001 Bethesda system. Terminology for reporting results of cervical cytology. JAMA. 2002; 287: 2114-2119). Statistically significant differences ($p<0.05$) and agreement between methods were analyzed using SAS v.9.3 statistical package.

Example 8

HPV Molecular Testing. Cervical samples in liquid preservative solution that underwent the enrichment process in view of Pap staining on the multiwell device, were also tested for HPV. HPV detection was performed on a fraction of the original specimen. Typically 100 µl of cell suspension were transferred to eppendorf tubes and centrifuged at 14,000 g for 10 min at RT. The cell pellets were resuspended in 500 µl of PBS and washed twice to remove preservative solution, then incubated in 75 µl of alkaline lysis buffer (25 mM NaOH, 0.2 mM Na EDTA) for 1 hr at 95° C. After cooling to RT, samples were neutralized in 75 µl of 40 mM Tris HCl pH8.3 and digested with 100 µg/ml of proteinase K for 2 hrs at 56° C. After enzyme inactivation by incubation at 96° C. for 10 min, samples were quickly spun, and 3 µl of supernatant used for PCR amplification.

Each sample was subjected to three parallel PCR reactions using type-specific primer pairs for HPV-16 and HPV-18, and the MY09/MY11 degenerate consensus primer pair annealing in a primer pair annealing in a highly conserved region of the HPV L1 gene (Manos M M, et al. The use of polymerase chain reaction amplification for the detection of genital human papillomaviruses. Cancer Cells. 1989; 7:209-214) and thus capable of amplifying a wide spectrum of HR-HPV subtypes (16, 18, 31, 33, 35, 39, 45, 51, 52, 56, 58, 59, 68). After 40 amplification cycles, PCR products were analyzed on 2% agarose gel and ethidium bromide stained to visualize fragments of 450 bp (HR-HPV), 390 bp (HPV-16) and 216 bp (HPV-18). CaSki and HeLa cell DNA were used as positive controls for HPV-16 and HPV-18 amplifications, respectively.

The Examples disclosed above are merely intended to illustrate the various utilities of this invention. It is understood that numerous modifications and variations of the present invention are possible in light of the above teachings and, therefore, within the scope of the appended claims, the present invention may be practiced otherwise than as particularly disclosed.

All patents and publications are herein incorporated for reference to the same extent as if each individual publication was specifically and individually indicated to be incorporated by reference. It should be understood that although the present invention has been specifically disclosed by preferred embodiments and optional features, modification and variation of the concepts herein disclosed may be resorted to by those skilled in the art, and that such modifications and variations are considered to be within the scope of this invention.

The invention claimed is:

1. A device for screening for abnormal cells in each of a plurality of patient cervical cell samples comprising:
   a multi-well plate comprising a plurality of delimited areas, wherein each delimited area is created from a coating and delineated by an edge formed by a thickness of the coating on the plate and sized to contain a population of cells for Papanicolau screening, such that an individual area contains the sample of a single patient; and
   a population of cervical cells from an individual patient adhered to each of the plurality of delimited areas of the plate to yield a plurality of cervical cell monolayers, wherein each monolayer is derived from an individual patient and each monolayer is adhered to an individual delimited area to prevent cross contamination.

2. The screening device of claim 1, further comprising Papanicolau staining reagents applied to each of the plurality of individual delimited areas of the plate.

3. The screening device of claim 1, further comprising a duplicate sample from each of the plurality of individual patient samples adhered to into a separate, delimited area of a plate to avoid cross contamination.

4. The screening device of claim 1 further comprising a monoclonal antibody specific for cervical disease disposed in the plurality of separate delimited areas of the plate.

5. The screening device of claim 4, wherein the monoclonal antibody is specific for an antigen selected from the group consisting of p16 (INK4a), Ki-67, and human papilloma virus and combinations thereof.

6. The screening device of claim 1, further comprising an identifier correlating delimited areas to an identity of the patient who is a source of the cell sample.

7. The screening device of claim 1, further comprising a device for measurement of optical density by a colorimetric reading.

8. The screening device of claim 1, further comprising a device for examination of each individual delimited area under magnification.

9. The screening device of claim 1, further comprising reagents for peroxidase inactivation.

10. The screening device of claim 1 wherein each individual delimited area is comprised of a constant number of cervical cells forming the monolayer.

* * * * *